(12) United States Patent
Imam et al.

(10) Patent No.: US 11,976,315 B2
(45) Date of Patent: May 7, 2024

(54) RECOMBINANT ALGAE HAVING HIGH LIPID PRODUCTIVITY

(71) Applicant: Viridos, Inc., La Jolla, CA (US)

(72) Inventors: Saheed Imam, La Jolla, CA (US); Eric R. Moellering, San Diego, CA (US); Luke Peach, La Jolla, CA (US); William F. Lambert, San Diego, CA (US); Kathleen Kwok, La Jolla, CA (US)

(73) Assignee: Viridos, Inc., La Jolla, CA (US)

( * ) Notice: Subject to any disclaimer, the term of this patent is extended or adjusted under 35 U.S.C. 154(b) by 0 days.

(21) Appl. No.: 17/519,383

(22) Filed: Nov. 4, 2021

(65) Prior Publication Data

US 2022/0136017 A1 May 5, 2022

Related U.S. Application Data

(60) Provisional application No. 63/110,301, filed on Nov. 5, 2020.

(51) Int. Cl.
| | | |
|---|---|---|
| *C12P 7/64* | (2022.01) | |
| *C07K 14/405* | (2006.01) | |
| *C12N 1/12* | (2006.01) | |

(52) U.S. Cl.
CPC .............. *C12P 7/64* (2013.01); *C07K 14/405* (2013.01); *C12N 1/125* (2021.05)

(58) Field of Classification Search
None
See application file for complete search history.

(56) References Cited

U.S. PATENT DOCUMENTS

2016/0273061 A1 9/2016 Hayakawa et al.
2018/0371401 A1 12/2018 Harayama et al.

FOREIGN PATENT DOCUMENTS

WO  WO 2021/126987 A1  6/2021

OTHER PUBLICATIONS

Chica et al. Curr Opin Biotechnol. Aug. 2005; 16(4):378-84. (Year: 2005).*
Singh et al. Curr Protein Pept Sci. 2017, 18, 1-11 (Year: 2017).*
PCT International Search Report and Written Opinion in International Application No. PCT/US2021/058092, dated Mar. 25, 2022, 11 pages.

* cited by examiner

*Primary Examiner* — Christian L Fronda
(74) *Attorney, Agent, or Firm* — DLA Piper LLP (US)

(57) ABSTRACT

The invention provides recombinant algal mutants that have a genetic modification to a gene or nucleic acid sequence encoding a WD40 repeat containing protein or domain. The genetic modification of one or more nucleic acid sequences encoding a WD40 repeat containing protein or domain results in a mutant organism with increased lipid productivity and/or higher biomass productivity (as measured by total organic carbon). The genetic modification can be a gene attenuation or functional deletion. The lipid products of these mutants can be utilized as biofuels or for other specialty chemical products. Methods of making and using the recombinant algal mutants and methods of producing lipids are also disclosed.

18 Claims, 8 Drawing Sheets

Figure 1A:
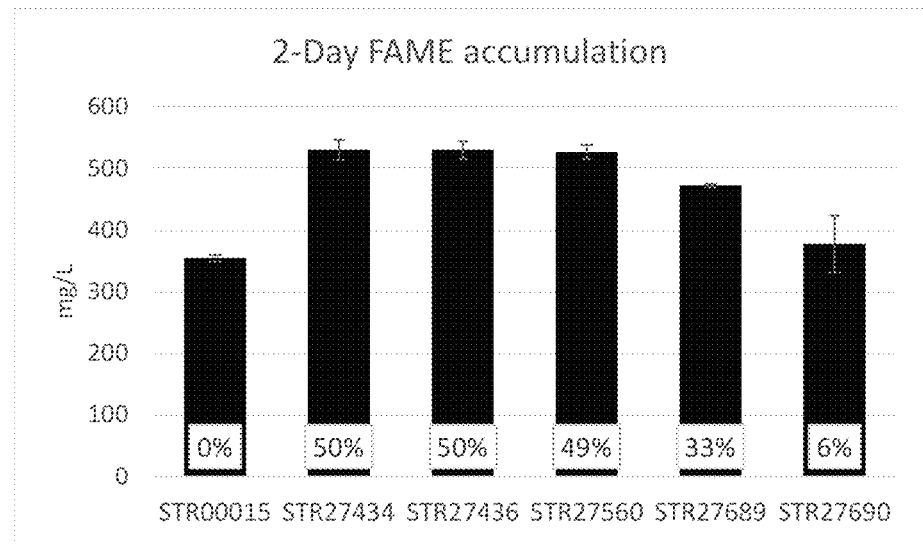

Specification includes a Sequence Listing.

FIG. 4A
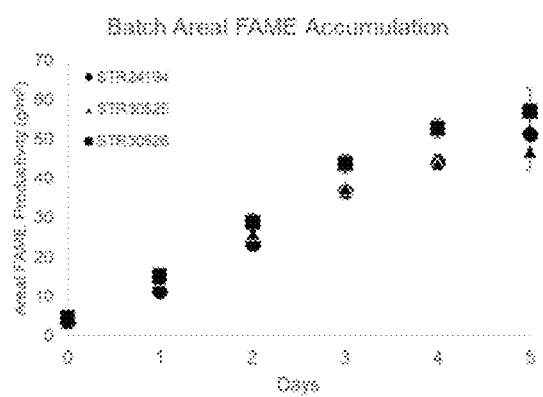
FIG. 4B
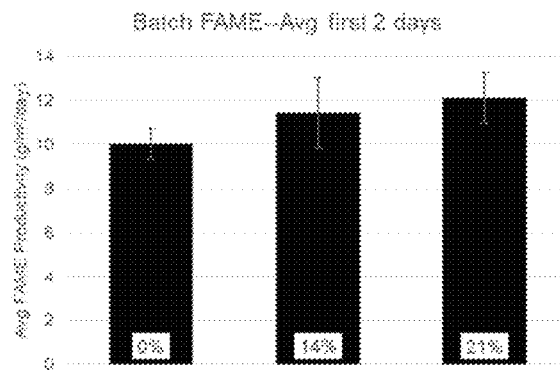
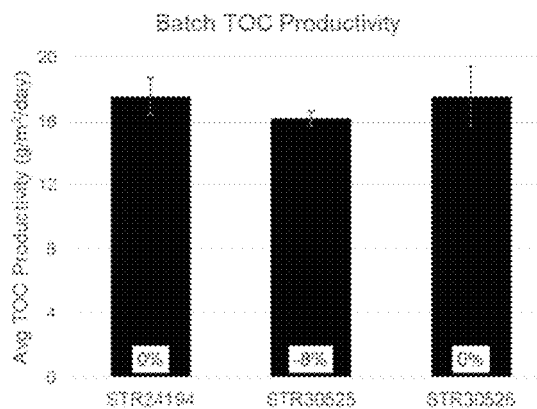
FIG. 4C
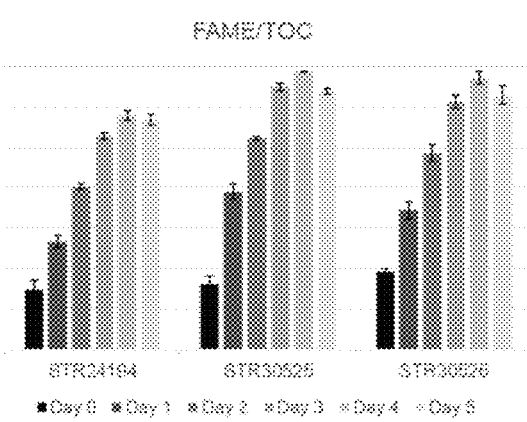
FIG. 4D

FIG. 5

RECOMBINANT ALGAE HAVING HIGH LIPID PRODUCTIVITY

CROSS-REFERENCE TO RELATED APPLICATIONS

This application claims benefit of priority under 35 U.S.C. § 119(e) of U.S. Ser. No. 63/110,301, filed Nov. 5, 2020, the entire contents of which is incorporated herein by reference in its entirety.

INCORPORATION OF SEQUENCE LISTING

The material in the accompanying sequence listing is hereby incorporated by reference into this application. The accompanying sequence listing text file, name SGI2290-1_Sequence_Listing.txt, was created on Nov. 4, 2021, and is 83.2 kb. The file can be accessed using Microsoft Word on a computer that uses Windows OS.

FIELD OF THE INVENTION

The invention involves the provision of a recombinant algal mutant organism and methods for the production of lipids.

BACKGROUND OF THE INVENTION

The production of biofuels presents great opportunities to develop environmentally sound sources of energy that can be obtained at reasonable cost. Efforts have been directed towards using algae or other microorganisms to produce hydrocarbons that can be used as biodiesel or other biofuels due to their high lipid content. Additional specialty chemicals can also be obtained from these organisms and for use in consumer products.

Since algae use energy from sunlight to combine water and carbon dioxide to produce biomass, achieving increased productivity offers the possibility of a carbon neutral fuel source. The development of algal strains with very high lipid productivity for the production of algal-sourced biofuels therefore presents the possibility of a significant reduction in new carbon dioxide released into the atmosphere and a consequent reduction in the problem of global warming.

The development of commercially viable algal biofuels requires strains with high lipid and biomass productivity. Even the most productive wild type strains are not sufficiently productive to permit an economically viable development of this resource. Strategies for increasing algal production of biofuels and other products have included modification of nutrition provided to the organisms, such as cultivating the organisms in nitrogen, phosphorus, or silicon deficient media. Other strategies have included modification of cultivation conditions or environmental protocols, or various efforts directed towards genetic engineering of the organisms. While engineering algae strains to have a combination of increased photosynthetic efficiency (resulting in increased overall biomass productivity) and/or high lipid productivity could provide a solution to this problem, deficiencies still remain. The development of more productive strains continues to be a barrier to efficient utilization of this energy source.

SUMMARY OF THE INVENTION

The invention provides recombinant algal mutants that have a genetic modification to a gene or nucleic acid sequence encoding a WD40 repeat containing protein. The genetic modification of one or more nucleic acid sequences encoding a WD40 repeat containing protein results in a mutant organism with increased lipid productivity and/or higher biomass productivity (as measured by total organic carbon). In some embodiments the genetic modification is a gene attenuation, or a deletion, disruption, or inactivation. The lipid products of these mutants can be utilized as biofuels or for other specialty chemical products. Methods of making and using the recombinant algal mutants and methods of producing lipids are also disclosed.

In a first aspect the invention provides a recombinant algal organism having a genetic modification in a gene or nucleic acid sequence encoding a WD40 repeat containing protein. The recombinant alga exhibits higher lipid productivity and/or higher biomass productivity versus a corresponding control algal cell not having the genetic modification. In one embodiment the recombinant alga is a Chlorophyte alga, which optionally can be of the Class Trebouxiophyceae. The gene or nucleic acid sequence encoding the WD40 repeat containing protein can have a nucleic acid sequence having at least 75% sequence identity to a nucleic acid sequence of any one of SEQ ID NOs: 14-26. In one embodiment the gene encoding the WD40 repeat containing protein has a nucleic acid sequence having at least 75% sequence identity to a nucleic acid sequence of SEQ ID NO: 15 or 16.

In one embodiment the genetic modification to the gene encoding the WD40 repeat containing protein is a functional deletion. The genetic modification of the gene encoding the WD40 repeat containing protein can result in an attenuation in the expression of the nucleic acid sequence. In one embodiment the genetic modification of the gene encoding the WD40 repeat containing protein is a deletion of one or more amino acids in a polypeptide sequence of a WD40 repeat containing protein. In one embodiment the genetic modification of the gene encoding the WD repeat containing protein is a frame shift mutation. The genetic modification can also be a deletion, a disruption, or an inactivation.

In one embodiment the recombinant alga has at least 30% higher lipid productivity versus a corresponding control alga that does not comprise the genetic modification. The recombinant alga can have at least 15% higher biomass productivity as measured by total organic carbon versus a control alga that does not comprise the genetic modification. The recombinant alga can exhibit at least 40 grams per square meter per day of lipid production after 5 days of cultivation.

In various embodiments the recombinant alga can higher biomass productivity per unit time as measured by production of total organic carbon (TOC). The recombinant alga can have higher biomass productivity under nitrogen deficient conditions. The recombinant alga can have higher total organic carbon production under nitrogen deficient conditions. In some embodiments the recombinant alga is of a family selected from Oocystaceae, Chlorellaceae, and Eustigmatophyceae; and the recombinant alga can be of a genus selected from *Chlorella*, *Parachlorella*, *Picochlorum*, *Tetraselmis*, and *Oocystis*.

In another aspect the invention provides a lipid containing product produced by any of the recombinant algae described herein.

In another aspect the invention provides a biomass product containing any of the recombinant algae described herein.

In another aspect the invention provides a method of producing a composition containing lipids. The methods involve cultivating a recombinant alga described herein and thereby producing a composition containing lipids. The method can also involve harvesting a lipidic composition from the recombinant alga. The method can involve producing a genetic modifications to a nucleic acid sequence encoding a WD repeat protein, which can be a functional deletion. The functional deletion can be obtained by subjecting the algal organism to ultra-violet light. In some embodiments the gene encoding the WD repeat containing protein has a nucleic acid sequence having at least 90% sequence identity to SEQ ID NO: 16. The algal organism can be a Chlorophyte alga, optionally of the genus *Oocystis*, but can be any recombinant alga described herein. The recombinant alga produced by the method can have at least 30% greater lipid productivity versus a control alga.

In another aspect the invention provides a method of producing a composition containing lipids. The methods involve performing a genetic modification to an algal organism in a gene encoding a WD40 repeat containing protein, and culturing the organism to thereby produce a composition containing lipids. The method can further involve harvesting a lipidic composition from the algal organism.

In another aspect the invention provides a method for identifying a recombinant algal organism with high lipid productivity and/or high biomass productivity. The method involves mutagenizing a population of algal organisms; screening the mutagenized algal organisms for higher lipid productivity; sequencing at least a portion of the genome of the mutagenized algal organisms; identifying genetic changes in the mutagenized organisms compared to the population of algal organisms prior to mutagenesis; recapitulating the genetic changes in a parental strain of the mutagenized algal organisms; and thereby identifying a recombinant algal organism having high lipid productivity. The method can further involve harvesting a lipidic composition from the recombinant algal organism. The recombinant algal organism with high lipid productivity and/or high biomass productivity can be any recombinant algal organism described herein. In one embodiment the recombinant algal organism can have at least 40% greater lipid productivity versus a control alga.

The summary of the invention described above is not limiting and other features and advantages of the invention will be apparent from the following detailed description of the invention, and from the claims. Section headings or sub-headings are provided solely for the convenience of the reader, and do not denote a departure from discussion or necessarily an entirely new subject matter area. Any subject matter can be discussed or disclosed under any section heading or sub-heading.

DETAILED DESCRIPTION OF THE DRAWINGS

Figure 1B:
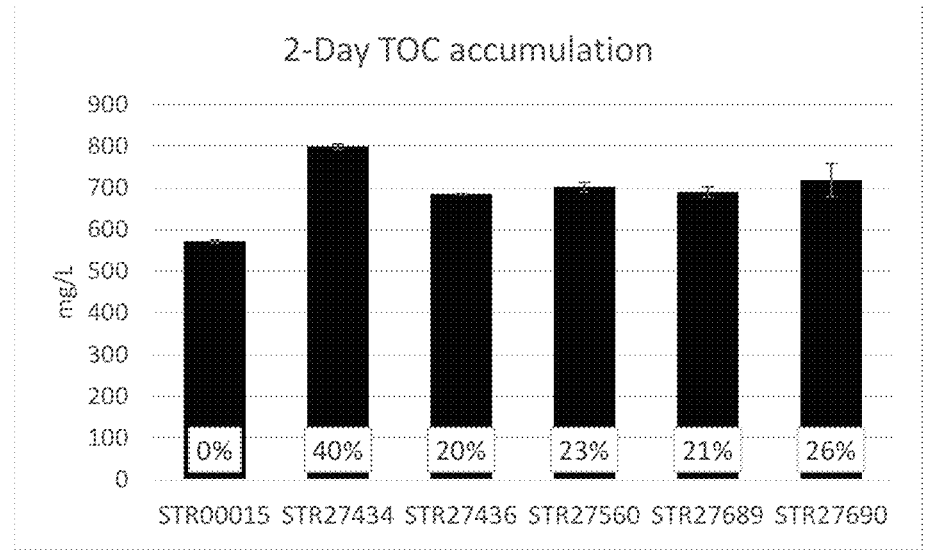
Figure 1C:
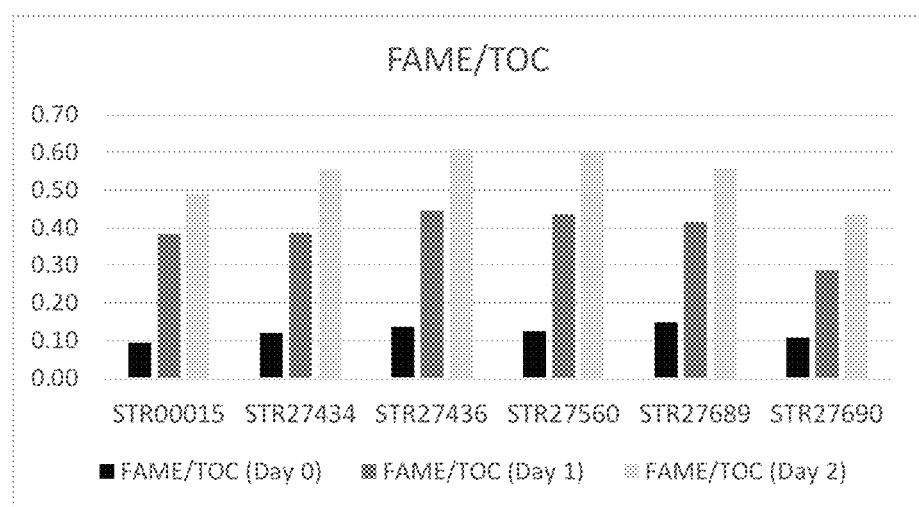

FIGS. 1A-1C are graphical illustrations of the effects on FAME and TOC accumulation in strains having a genetic modification to a nucleic acid sequence encoding a WD40 repeat family protein by mutagenesis of wild type cells (Strain 15). FIG. 1A shows 2-day FAME accumulation for various *Oocystis* strains. FIG. 1B shows 2-day TOC accumulation. FIG. 1C shows the ratio of FAME/TOC for various strains as an indicator of carbon partitioning. Mutagenized strains include 27434, 27436, 27550, 27689, and 27690, which all contain a deletion to SEQ ID NO: 1 (a WD40 repeat containing protein). The 2-day data was measured after 48 hours of growth in nitrogen deplete media.

Figure 2A:
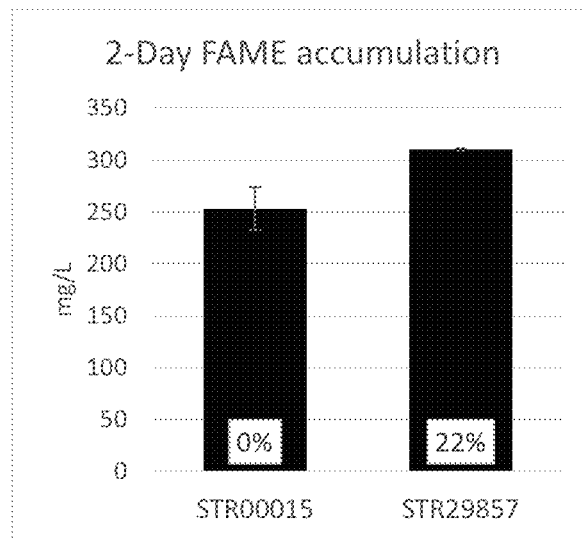
Figure 2B:
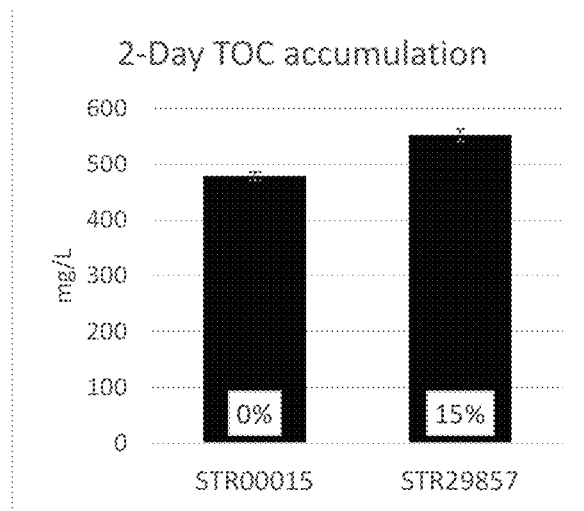
Figure 2C:
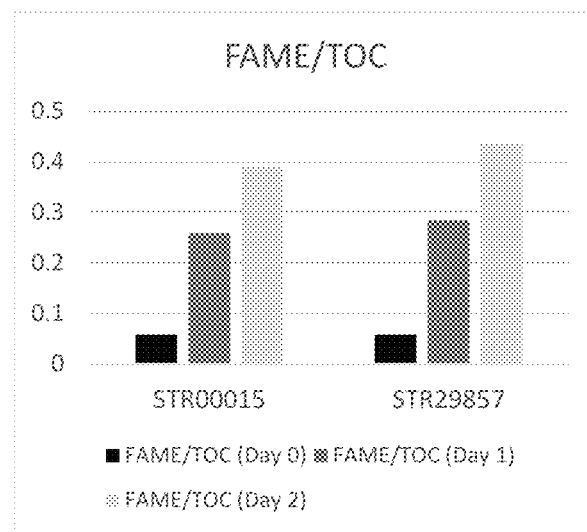

FIGS. 2A-2C are graphical illustrations of the FAME and TOC accumulation in wild type strains constructed to have a deletion of a nucleic acid sequence encoding a WD40 repeat family protein. FIG. 2A shows 2-day FAME accumulation for modified *Oocystis* sp. strains (29857) versus the wild type (Strain 15). FIG. 2B shows 2-day TOC accumulation. FIG. 2C shows the ratio of FAME/TOC, a useful measure of carbon partitioning.

Figure 3A:
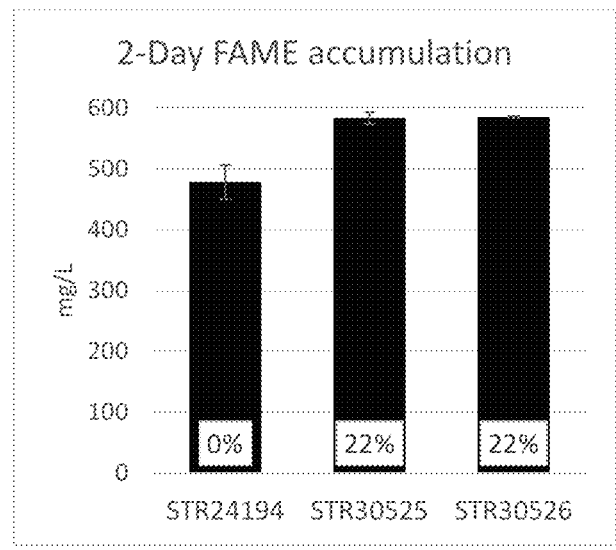
Figure 3B:
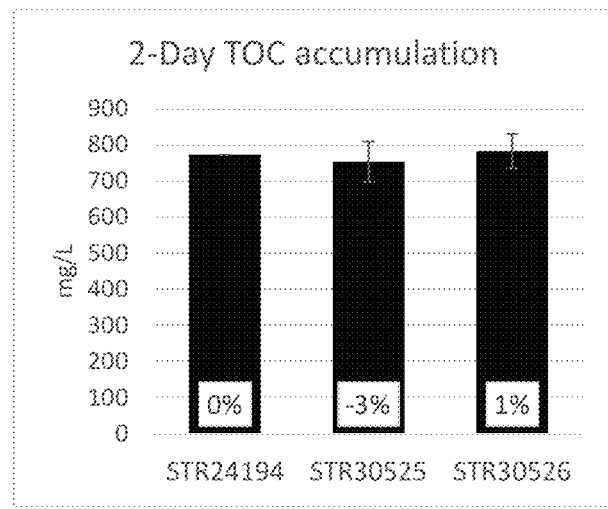
Figure 3C:
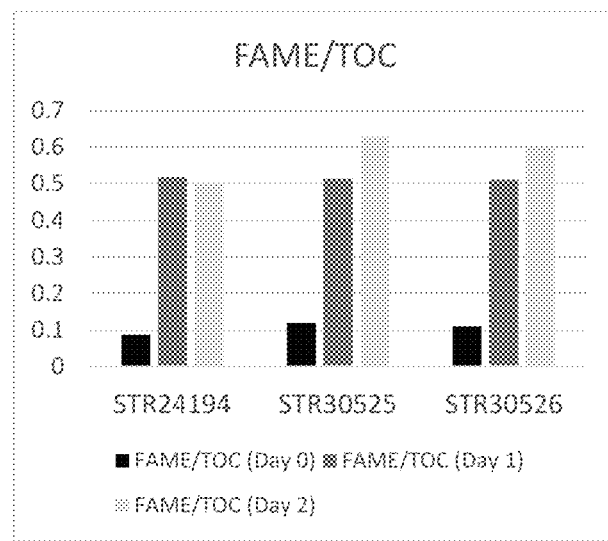

FIGS. 3A-3C are graphical illustrations of the FAME and TOC accumulation in a laboratory strain (24194) constructed to have a deletion of a nucleic acid sequence encoding a WD40 repeat family protein versus the (control) laboratory strain. FIG. 3A shows 2-day FAME accumulation for the laboratory strain (Strain 24194) and modified *Oocystis* sp. strains (30525 and 30526). FIG. 3B shows 2-day TOC accumulation. FIG. 3C shows the ratio of FAME/TOC, a useful measure of carbon partitioning.

FIGS. 4A-4D provide a graphical illustration of 5-day data for FAME and TOC productivity under nitrogen deplete conditions. FIG. 4A shows areal FAME productivity v. days. FIG. 4B shows average FAME productivity for the first 2 days. FIG. 4C shows TOC productivity. And FIG. 4D shows the FAME/TOC ratios over a 5 day period.

FIG. 5 is a sequence alignment of protein sequences of various Chlorophyte algae species. It is shown that there is a high degree of sequence identity across Chlorophyte species in key domains of the polypeptide sequence.

DETAILED DESCRIPTION OF THE INVENTION

The invention provides recombinant algal mutants that have a genetic modification to a nucleic acid sequence encoding a WD40 repeat containing protein. The genetic modification(s) described herein result in a recombinant or mutant cell or organism with higher lipid productivity and/or higher biomass productivity. The recombinant algal mutants can also optionally have reduced chlorophyll content and/or a reduced PSII antenna size versus a corresponding control cell or organism not having the genetic modification. In various embodiments the genetic modification(s) described herein can result in substantial increases in lipid productivity and/or biomass productivity. Any of the recombinant cells or organisms disclosed herein can be mutant photosynthetic organisms.

The recombinant cell or organism of the invention having a genetic modification described herein can have higher lipid productivity and/or higher biomass productivity than a corresponding (control) cell or organism. In some embodiments the genetic modification is an attenuation of a gene or nucleic acid sequence encoding a WD40 repeat containing protein. In any embodiment lipid productivity can be measured by FAME accumulation, and biomass productivity can be measured as the rate of biomass accumulation, for example as the total organic carbon (TOC) content of the respective cells or organisms.

In one embodiment the mutant or recombinant algal cell or organism has higher lipid and/or biomass productivity in batch culture compared to a corresponding (control) cell or organism not having the genetic modification. Batch culture is a culture where nutrients are not renewed or re-supplied to the medium during the time period the cells or organisms are cultured. In other embodiments the mutant or recombinant algal cell or organism has higher lipid and/or biomass productivity under nitrogen deplete conditions compared to a corresponding (control) cell or organism. In some embodiments the higher lipid and/or biomass productivity is achieved under batch culture and nitrogen deplete conditions; and in other embodiments the higher lipid and/or biomass productivity is achieved under semi-continuous or continuous culture conditions. Semi-continuous culture conditions are conditions where a fixed volume of culture is removed at regular time intervals and an equal volume of fresh medium is immediately added back to the culture. In various embodiments the fixed volume removed and added is from 10% to 90% of the total culture volume. Continuous culture conditions involve regular removal of culture with immediate replacement with fresh medium. Persons of ordinary skill realize that time intervals can vary with the purpose of the culture and continuous culture conditions involve a more frequent removal of culture and replacement with fresh medium than semi-continuous conditions.

Any of the mutant or recombinant cells or organisms disclosed herein can be photosynthetic cells or organisms. Any of the mutant or recombinant cells or organisms described herein can exhibit increased lipid productivity and/or increased biomass productivity under photoautotrophic conditions compared to a corresponding control cell or organism, i.e. conditions where the recombinant cells or organisms can produce their own biomass using light, carbon dioxide, water, and nutrients via photosynthesis. Corresponding (control) cells or organisms are useful for evaluating the effect of any one or more of the genetic modifications. Corresponding (control) cells or organisms do not have the one or more genetic modifications being evaluated and are subjected to the same or substantially the same conditions as the test cells or organisms such that a difference in the performance or characteristics of the cells or organisms is based only on the genetic modification(s) being evaluated. In any embodiment the corresponding (control) cells or organisms can be of the same species as the test organism. They can be derived from the same parent cell or parental line. They can also be the same or similar in every way except for the one or more genetic modification(s) being evaluated. In some embodiments the corresponding (control) cell or organism is a wild-type cell or organism. But the corresponding (control) cell or organism can also be a laboratory strain or parental strain of the test cell or organism. Substantially the same conditions can be the same conditions or slightly different conditions where the difference does not materially affect the function, activity, or expression of the nucleic acid sequence modified.

In various embodiments the recombinant cells or organisms are algal cells. In one embodiment the recombinant alga has a genetic modification to a gene encoding a WD40 repeat containing protein. The lipid products of these mutants can be further processed into biofuels or used in the production of other specialty chemical products. The gene or nucleic acid sequence encoding the WD40 repeat containing protein or domain that contains the genetic modification can encode any of the polypeptide sequences described herein, hereby disclosed in all possible combinations or sub-combinations as if set forth fully herein.

In some embodiments recombinant cells or organisms of the invention can have a reduced amount of chlorophyll b, and can have an increased chlorophyll a to chlorophyll b ratio (chl a/chl b) compared to a corresponding control cell or organism. The recombinant cells or organisms can have decreased photosynthetic antenna size, for example reduced photosystem II (PSII) and/or reduced photosystem I (PSI) antenna size. In various embodiments the cross-sectional unit size of the PSII and/or PSI antenna of the recombinant cells or organisms disclosed herein can be reduced by at least 10%, at least 20%, at least 30%, at least 25%, at least 30%, at least 35%, at least 40%, at least 45%, at least 50%, or at least 60% compared to the PSII and/or PSI antenna size of a corresponding control cell or organism.

In any embodiment the recombinant cells or organisms can have a higher growth rate and/or a higher biomass productivity than a corresponding control cell or organism not having the genetic modification, for example, higher biomass productivity per hour or per day or per period of 2 days or 3 days or 4 days or 5 days or 6 days. "Biomass" refers to cellular mass, whether of living or dead cells. Biomass productivity, or biomass accumulation, or growth rate, can be measured by any means accepted in the art, for example as ash free dry weight (AFDW), dry weight, wet weight, or total organic carbon (TOC) productivity. In any embodiment biomass productivity, or biomass accumulation, or the growth rate, can be measured as total organic carbon (TOC) productivity.

The recombinant cells or organisms of the invention can produce a greater amount of a bioproduct per time period (e.g. per minute or per hour or per day or per period of 2 days or 3 days or 4 days or 5 days or 6 days), for example a lipid product (which can optionally be measured as FAME), a fatty acid product, a carbohydrate, a protein product, or a polymer than a corresponding (control) organism not having the genetic modification(s). The amount of bioproduct can be expressed as g/time period, mg/time period, ug/time period, or any other defined quantity per defined time period described herein. Such bioproducts can be isolated from a lysate or biomass or cellular secretion of any of the recombinant cells or organisms of the invention. In some embodiments, the recombinant cells or organisms of the invention produce at least 10%, at least 15%, at least 20%, at least 25%, at least 30%, at least 35%, at least 40%, at least 45%, at least 50%, at least 60%, at least 70%, at least 80%, at least 90% or at least 100% more of a bioproduct than a corresponding control alga cultured under the substantially the same conditions, which can be batch, semi-continuous, or continuous culture conditions and may be nutrient replete culture conditions or may be nitrogen deplete conditions, and may be photoautotrophic conditions. In some embodiments the recombinant cells or organisms of the invention product at least 20% or at least 30% more lipid (e.g. as measured by FAME) over a 2-day period, or at least 30% or at least 40% more of a lipid product over a 5-day period.

Without wanting to be bound by any particular theory it is believed that the genetic modifications described herein result in an attenuation or partial or complete elimination of expression of a WD40 repeat containing protein. Such attenuation or elimination results in a significant increase in lipid productivity in the cell, which in one embodiment can be measured as the total FAME produced by the cell. A further result can be a significant increase in biomass productivity, which in one embodiment can be demonstrated by the organic carbon produced by the cell (as measured, for example, by total organic carbon).

As used herein, "exogenous" with respect to a nucleic acid or gene indicates that the nucleic acid or gene has been introduced (e.g. "transformed") into an organism, microorganism, or cell by human intervention. For example, such an exogenous nucleic acid can be introduced into a cell or organism via a recombinant nucleic acid construct. An exogenous nucleic acid can be a sequence from one species introduced into another species, i.e., a "heterologous" nucleic acid. A heterologous nucleic acid can also be an exogenous synthetic sequence not found in the species into which it is introduced. An exogenous nucleic acid can also be a sequence that is homologous to an organism (i.e., the nucleic acid sequence occurs naturally in that species or encodes a polypeptide that occurs naturally in the host species) that has been isolated and subsequently reintroduced into cells of that organism. In some embodiments an exogenous nucleic acid that includes a homologous sequence can be distinguished from the naturally-occurring sequence by the presence of non-natural sequences linked to the exogenous nucleic acid, which can include but are not limited to non-native regulatory sequences attached to the homologous gene sequence in a recombinant nucleic acid construct. Alternatively or in addition, a stably transformed exogenous nucleic acid can be detected and/or distinguished from a native gene by its juxtaposition to sequences in the genome where it has integrated. Further, a nucleic acid is considered exogenous if it has been introduced into a progenitor of the cell, organism, or strain under consideration.

A "recombinant" or "engineered" nucleic acid molecule is a nucleic acid molecule that has been altered through human manipulation. As non-limiting examples, a recombinant nucleic acid molecule includes any nucleic acid molecule that: 1) has been partially or fully synthesized or modified in vitro, for example, using chemical or enzymatic techniques (e.g., by use of chemical nucleic acid synthesis, or by use of enzymes for the replication, polymerization, digestion (exonucleolytic or endonucleolytic), ligation, reverse transcription, transcription, base modification (including, e.g., methylation), integration or recombination (including homologous and site-specific recombination) of nucleic acid molecules); 2) includes conjoined nucleotide sequences that are not conjoined in Nature; 3) has been engineered using molecular biology techniques such that it lacks one or more nucleotides with respect to the naturally occurring nucleic acid molecule sequence; and/or 4) has been manipulated using molecular biology techniques such that it has one or more sequence changes or rearrangements with respect to the naturally occurring nucleic acid sequence, or has a sequence (e.g. by insertion) not found in the naturally occurring nucleic acid sequence. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector.

When applied to organisms, the terms "transgenic" "transformed" or "recombinant" or "engineered" or "genetically engineered" refer to organisms that have been manipulated by introduction of an exogenous or recombinant nucleic acid sequence into the organism, or by genetic modification of native sequences (which are therefore then recombinant). Recombinant or genetically engineered organisms can also be organisms into which constructs for gene "knock down," deletion, attenuation, inactivation, or disruption have been introduced to perform the indicated manipulation. Such constructs include, but are not limited to, RNAi, microRNA, shRNA, antisense, and ribozyme constructs. A recombinant organism can also include those having an introduced exogenous regulatory sequence operably linked to an endogenous gene of the transgenic microorganism, which can enable transcription in the organism. Also included are organisms whose genomes have been altered by the activity of meganucleases or zinc finger nucleases. A heterologous or recombinant nucleic acid molecule can be integrated into a genetically engineered/recombinant organism's genome or, in other instances, not integrated into a recombinant/genetically engineered organism's genome, or can be present on a vector or other nucleic acid construct. As used herein, "recombinant microorganism" or "recombinant host cell" includes progeny or derivatives of the recombinant microorganisms of the disclosure.

Any of the recombinant algal cells or organisms described herein can be generated by human activity, for example, by classical mutagenesis and/or genetic engineering, but can also be produced by any feasible mutagenesis method, including but not limited to exposure to UV light, CRISPR/Cas9, cre/lox, gamma irradiation, or chemical mutagenesis. Screening methods can be used to identify mutants having desirable characteristics (e.g., reduced chlorophyll and increased lipid and/or biomass productivity). Methods for generating mutants of algal organisms using classical mutagenesis, genetic engineering, and phenotype or genotype screening are known in the art.

Algal Cell or Organism

The recombinant algal cell or organism of the invention can be a mutant microalga, or a mutant photosynthetic organism, or a mutant green alga. The recombinant alga can be any eukaryotic microalga such as, but not limited to, a Chlorophyte, an Ochrophyte, or a Charophyte alga. In some embodiments the mutant microalga can be a Chlorophyte alga of the taxonomic Class Chlorophyceace, or of the Class Chlorodendrophyceae, or the Class Prasinophyceace, or the Class Trebouxiophyceae, or the Class Eustigmatophyceae. In some embodiments, the mutant microalga can be a member of the Class Chlorophyceace, such as a species of any one or more of the genera *Asteromonas, Ankistrodesmus, Carteria, Chlamydomonas, Chlorococcum, Chlorogonium, Chrysosphaera, Dunaliella, Haematococcus, Monoraphidium, Neochloris, Oedogonium, Pelagomonas, Pleurococcus, Pyrobotrys, Scenedesmus,* or *Volvox*. In other embodiments the mutant microalga of the invention can be a member of the Order Chlorodendrales, or Chlorellales. In other embodiments, the mutant microalga can be a member of the Class Chlorodendrophyceae, such as a species of any one or more of the genera *Prasinocladus, Scherffelia,* or *Tetraselmis*. In further alternative embodiments, the mutant alga can be a member of the Class Prasinophyceace, optionally a species of any one or more of the genera *Ostreococcus* or *Micromonas*. Further alternatively, the mutant microalga can be a member of the Class Trebouxiophyceae, and optionally of the Order Chlorellales, and optionally a genera selected from any one or more of *Botryococcus, Chlorella, Auxenochlorella, Heveochlorella, Marinichlorella, Oocystis, Parachlorella, Pseudochlorella, Tetrachlorella, Eremosphaera, Franceia, Micractinium, Nannochloris, Picochlorum, Prototheca, Stichococcus,* or *Viridiella*, or any of all possible combinations or sub-combination of the genera. In another embodiment the recombinant alga can be a Chlorophyte alga of the Class Trebouxiophyceae and the family Coccomyxaceae, and the genus *Coccomyxa* (e.g. *Coccomyxa subelhpsoidea*). Or of the family Chlamydomonadaceae and the genus *Chlamydomonas* (e.g. *Chlamydomonas reinhardtii*); or of the family Volvocaceae and the genus *Volvox* (e.g. *Volvox carteri, Volvox aureus, Volvox globator*).

In another embodiment the recombinant alga is a Chlorophyte alga of the Class Trebouxiophyceae, or Eustigmatophyceae, and can be of the Order Chlorellales or Chlorodendrales, and can be of the Family Oocystaceae, or Chlorellaceae, or Monodopsidaceae, and optionally from a genus selected from any one or more of *Oocystis, Parachlorella, Picochlorum, Nannochloropsis,* and *Tetraselmis*, in all possible combinations and sub-combinations. The recombinant alga can also be from the genus *Oocystis*, or the genus *Parachlorella*, or the genus *Picochlorum*, or the genus *Tetraselmis*, or from any of all possible combinations and sub-combinations of the genera. In one embodiment the recombinant algal cell or organism is of the Class Trebouxiophyceae, of the Order Chlorellales, and optionally of the family Oocystaceae, and optionally can be of the genus *Oocystis*.

Genetic Modification

In various embodiments the recombinant alga of the invention can have a genetic modification disclosed herein to a gene encoding a WD40 repeat containing protein. In one embodiment the recombinant alga of the invention has a genetic modification to a gene encoding a WD40 repeat containing protein or domain. In one embodiment the genetic modification is to a native or endogenous sequence of the cell or organism.

A "genetic modification" applied in the invention can be any one or more of an attenuation, a deletion, a gene "knock out," a mutation, a disruption, an insertion, insertion of a stop codon, an inactivation, a rearrangement, one or more point mutations, a frameshift mutation, a nonsense mutation, an inversion, a single nucleotide polymorphism (SNP), a truncation, a point mutation, that changes the activity or expression of the one or more gene or nucleic acids. In some embodiments the change in expression is a reduction in expression or an elimination of the expression or activity, which expression can be the production of an encoded protein. The genetic modification can be made or be present in any sequence that affects expression or activity of the gene or nucleic acid sequence, or the nature or quantity of its product, for example to a coding or non-coding sequence, a promoter, a terminator, an exon, an intron, a 3' or 5' UTR, or other regulatory sequence. A genetic modification can be performed in any structure of the gene that results in attenuation or elimination of the gene or nucleic acid product or activity. In one embodiment the genetic modification is a deletion, disruption, or inactivation. The genetic modification can be made to, or be present in, the host cell's native genome. In some embodiments, a recombinant cell or organism having attenuated expression of a gene as disclosed herein can have one or more mutations, which can be one or more nucleobase changes and/or one or more nucleobase deletions and/or one or more nucleobase insertions, into the region of a gene 5' of the transcriptional start site, such as, in non-limiting examples, within about 2 kb, within about 1.5 kb, within about 1 kb, or within about 0.5 kb of the known or putative transcriptional start site, or within about 3 kb, within about 2.5 kb, within about 2 kb, within about 1.5 kb, within about 1 kb, or within about 0.5 kb of the translational start site. The genetic modification can comprise the deletion of one or more amino acids in a polypeptide sequence of a WD40 repeat containing protein.

A frameshift mutation is a particular type of mutation that involves either insertion or deletion of bases of DNA, where the number of inserted or deleted bases is not divisible by three. As a result a frameshift mutation disrupts the natural codon reading frame. This can result in insertion of an amino acid other than the naturally occurring programmed amino acid. Some or all of the entire DNA sequence following the mutation can also be disrupted or read incorrectly, i.e. as programming an amino acid other than the naturally programmed amino acid. In some embodiments a frame shift mutation can result in premature termination of translation. Thus, in such embodiments the encoded polypeptide sequence can be much shorter, and unable to accomplish its natural function in the cell or organism. Thus, the gene or nucleic acid sequence has been functionally deleted. A nonsense mutation is the substitution of one or more base pair(s) that leads to a stop codon being inserted into a nucleic acid sequence. As a result, a nonsense mutation results in premature termination of translation, and can mean the functional deletion of the gene or nucleic acid sequence.

An "attenuation" is a genetic modification resulting in a reduction of the function, activity, or expression of a gene or nucleic acid sequence compared to a corresponding (control) cell or organism not having the genetic modification being examined, i.e. the diminished function, activity, or expression is due to the genetic modification. The activity of a nucleic acid sequence can be expression of an encoded polypeptide, a binding activity, the amount of signal transduction or transcription regulation, or other activity the nucleic acid sequence exerts within the organism. In various embodiments an attenuated gene or nucleic acid sequence disclosed herein produces less than 90%, or less than 80%, or less than 70%, or less than 50%, or less than 30%, or less than 20%, or less than 10%, or less than 5% or less than 1% of its function, activity, or expression of the gene or nucleic acid sequence compared to the corresponding (control) cell or organism. In various embodiments a gene attenuation can be achieved via a deletion, a disruption, or an inactivation. Any of the genetic modifications described herein can result in partial or complete attenuation of the function, activity, or expression of the attenuated gene or nucleic acid sequence, which in some embodiments can lead to a level of function, activity, or expression that is not substantially more than that of complete attenuation; for example, the function, activity, or expression can yield a result that is less than 10% different from a recombinant cell or organism having a complete attenuation of the gene or nucleic acid sequence.

An unmodified gene or nucleic acid sequence present naturally in the organism denotes a natural, endogenous, or wild type sequence. A deletion can mean that at least part of the object nucleic acid sequence is deleted or that at least part of the encoded product is eliminated. But a deletion can also be accomplished by disrupting a gene through, for example, the insertion of a sequence into the gene that is not naturally present (e.g. a selection marker), a combination of deletion and insertion, or mutagenesis resulting in insertion of a stop codon. But a deletion can also be performed by other genetic modifications known to those of ordinary skill that result in the loss of expression, activity, or function of a gene or nucleic acid sequence.

A functional deletion is a genetic modification that removes at least so much of the activity or expression of a gene or nucleic acid sequence so that any remaining activity or expression of the gene or nucleic acid sequence has no significant effect on the cell or organism compared to a corresponding (control) cell or organism not having the functional deletion and cultivated under the same or substantially the same conditions. In some embodiments the functional deletion can remove all function, activity, or expression of the gene or nucleic acid sequence. A functional deletion can involve an at least partial deletion of the coding or non-coding sequence of the gene. A "deletion" or "knock out" removes all function, activity, or expression of a gene or nucleic acid sequence. A "disruption" of a gene is a functional deletion by insertion or deletion of a nucleotide sequence into or from the coding, non-coding, or regulatory portion of a gene with resulting partial or complete loss of function, activity, or expression of the gene. An "inactivation" is a type of functional deletion causing partial or complete loss of activity or expression of an inactivated gene or nucleic acid sequence. An "inactivation" can be reversible or irreversible (for example the reversible or irreversible binding of a component to the gene or nucleic acid sequence). Thus, deletions, functional deletions, inactivations, and disruptions can also be attenuations; disruptions and inactivations can also be functional, i.e. can remove at least so much of the activity or expression of a gene or nucleic acid sequence so that any remaining activity or expression of the gene or nucleic acid sequence has no significant effect on the cell or organism compared to a corresponding (control) cell or organism. An attenuation can also be a downregulation of a gene or nucleic acid sequence, which refers to the cell or organism decreasing the amount of function, activity, or expression. Functional expression refers to the expression of a functional product or activity of a nucleic acid sequence. When the expressed product of a nucleic acid is a polypeptide, functional expression means expression of polypeptide activity having at least 10% or at least 25% or at least 50% or at least 75% of the activity of a corresponding (control) cell or organism not having the modification and cultivated under the same or substantially the same conditions. For activity of a gene or nucleic acid sequence functional expression means activity or expression of at least 10% or at least 25% or at least 50% or at least 75% of the activity or expression of a corresponding (control) cell or organism not having the modification at issue and cultivated under the same or substantially the same conditions. Thus, various types of genetic modifications can be given terms that overlap in description. Persons of ordinary skill know that the particular term describing a genetic modification can be dependent both on how a gene or its components, or nucleic acid sequence is being physically changed as well as on the context. The recombinant cells or organisms of the invention can have any of the types of genetic modifications described herein.

In one embodiment the genetic modification is a deletion (or "knock out") involving the introduction of a stop codon into a gene or nucleic acid sequence encoding a WD40 repeat containing protein described herein or variant thereof. For example the genetic modification can be a stop codon or frame shift mutation (or other genetic modification described herein) introduced into a gene or nucleic acid of any one of SEQ ID NO: 14-26 or a variant of any, or in a gene or nucleic acid sequence encoding any one of SEQ ID NOs: 1-13 (WD40 repeat containing proteins), or a variant of any. In one embodiment the genetic modification is a stop codon or frame shift mutation inserted into a gene or nucleic acid sequence of SEQ ID NO: 15 or 16 or a variant of either, or encoding SEQ ID NO: 1, or a variant thereof. In another embodiment the genetic modification is a stop codon or frame shift mutation inserted into a gene or nucleic acid sequence encoding SEQ ID NO: 8, or a variant thereof (WD40 repeat containing protein of *Parachlorella*). Variant sequences of any sequence described herein have at least 60% sequence identity or at least 70% sequence identity or at least 75% or at least 80% or at least 85% or at least 90% or at least 95% or at least 98% sequence identity to any nucleotide or polypeptide sequence of any of SEQ ID NOs: 1-26. In some embodiments a variant sequence can also have at least 25 or at least 50 or at least 75 or at least 100 or at least 150 or at least 200 or at least 250 or at least 300 or at least 350 or at least 400 contiguous amino acids of any one of SEQ ID NOs: 1-13, and optionally, also have a recited percent identity. In other embodiments the variants sequence can have at least 500 or at least 600 or at least 700 or at least 800 or at least 1000 or at least 1200 or at least 1400 or at least 1500 contiguous nucleotides of any sequence of SEQ ID NO: 14-26 and, optionally, also have a recited percent identity.

In one embodiment the genetic modification is a modification that results in a stop codon, nonsense mutation, or frame shift mutation (or other genetic modification described herein) at the sequence coding for SEQ ID NO: 14 (AGACTCGCACCG) (V204fs), or a variant thereof, or in SEQ ID NO: 15 or 16, or a variant of either. The genetic modification can also be targeted to a regulatory sequence with the effect of eliminating or diminishing the activity or expression of a gene or nucleic acid sequence of SEQ ID NO: 14-26 or a variant of any, or a gene or nucleic acid sequence that encodes for any one SEQ ID NO: 1-13 or a variant of any of them.

In some embodiments the genetic modification can also be a frame shift mutation, a stop codon mutation, or a nonsense mutation introduced into a gene or nucleic acid sequence (including regulatory sequences supporting such gene or nucleic acid sequences) encoding any WD40 repeat containing protein disclosed herein. In various embodiments the gene or nucleic acid sequence is of SEQ ID NO: 14-26, or a variant of any; in a specific embodiment the gene or nucleic acid sequence encodes for a polypeptide of SEQ ID NO: 1 (or a variant thereof) or a polypeptide of SEQ ID NO: 8 (or a variant thereof), which mutation can be introduced at any location of the sequence or into a regulatory sequence governing the sequence, where the modification results in a termination of transcription from the gene prior to its natural point. Thus, in one embodiment the mutation is the introduction of a frame shift mutation, stop codon, or nonsense mutation that functionally deletes or disrupts the activity or expression of the gene or nucleic acid sequence. The frame shift mutation, stop codon, or nonsense mutation (or other modification) can also be introduced at any of many different loci or locations within a gene encoding a WD40 repeat containing protein or in a regulatory sequence, for example at a promoter, terminator or other regulatory sequence, that attenuates the gene or the activity of the encoded polypeptide, and that results in functional deletion of the gene. Analogous modifications can be made to the sequence(s) for similar effect. Such insertion or deletion or other mutation can also cause a loss of expression, function or activity in the encoded WD40 repeat containing protein, and result in the effect of increased lipid productivity.

In other embodiments the genetic modification can be to a nucleic acid sequence of SEQ ID NO: 15 or 16, or to a variant of either having at least 70% sequence identity or at least 75% or at least 80% or at least 85% or at least 90% or at least 95% or at least 98% sequence identity to any nucleotide sequence of SEQ ID NOs: 15 or 16.

Any of the recombinant cells or organisms of the invention can have a reduced functional absorption cross section of PSII and/or reduced PSII antenna size. For example, the cross-sectional unit size of the PSII antenna can be reduced by at least about 10%, at least 20%, at least 30%, at least 25%, at least 30%, at least 35%, at least 40%, at least 45%, at least 50%, at least 60%, at least about 70%, or at least about 80% compared to the functional absorption cross section of PSII and/or PSII antenna size of the corresponding (control) cell or organism not having the genetic modification. In some embodiments the recombinant cells or organisms of the invention can additionally (and optionally) have a reduced functional absorption cross section of PSI or reduced PSI antenna size by the same amounts stated above versus a corresponding (control) cell or organism. All statements herein of increases in biochemical parameters (e.g. FAME productivity or TOC productivity) are versus a corresponding (control) cell or organism unless indicated otherwise.

In some embodiments, a recombinant algal cell or organism as provided herein can have increased Fv/Fm with respect to a corresponding control cell or organism. For example, the mutant photosynthetic organism may have Fv/Fm increased by at least 5%, at least 10%, at least 12%, at least 15%, at least 20%, at least 30%, at least 40% or at least 50% compared to a corresponding (control) photosynthetic organism. In various embodiments the Fv/Fm can be increased by 5-50%, or by 5-30% or by 5-20% with respect to a control photosynthetic organism.

Further, a mutant photosynthetic organism as provided herein can have an increased rate of electron transport on the acceptor side of photosystem II with respect to a control or wild type cell. The rate can be at least about 20%, 30%, 40%, 50%, 60%, 80%, or 100% higher compared to a corresponding control cell or organism. In addition, mutant photosynthetic cells or organisms of the invention can have a rate of carbon fixation (Pmax (C)) in a recombinant cell or organism as provided herein can be elevated with respect to a control organism. For example, Pmax (14C) can be increased by at least about 20%, 30%, 40%, 50%, 60%, 80%, or 100% compared to a corresponding control cell or organism.

In some embodiments, the recombinant cells or organisms of the invention have decreased PSI and/or PSII antenna size and can optionally also have a higher amount of a ribulose bisphosphate carboxylase activase (Rubisco activase or "RA") than a corresponding (control) or wild type organism, for example, at least 1.2, 1.4, 1.6, 1.8, 2, 2.2, or 2.5 fold the amount of RA as a control organism. In some embodiments, the mutants demonstrate reduced expression of 6, 8, 10, 12, or 14 LHCP genes and increased expression of an RA gene, such as an RA-a or RA-P gene. Thus, the recombinant cells or organisms of the invention can be mutant photosynthetic organisms having reduced chlorophyll and reduced PSII antenna size where the mutants have a higher amount of Rubisco activase than control photosynthetic organisms.

The LHC super-gene family encodes the light-harvesting chlorophyll a/b-binding (LHC) proteins that constitute the antenna system of the photosynthetic apparatus. A recombinant algal mutant of the invention can also have a reduced expression of one or more LHC genes. Thus, in some embodiments the recombinant cells or organisms of the invention have at least 6, at least 8, at least 10, or at least 12 LHC genes that are attenuated or downregulated with respect to their expression level in a corresponding (control) cell or organism. In various embodiments the reduction in expression of the one or more LHC genes can be a reduction of at least 20%, or at least 30%, or at least 40%, or at least 50%, or at least 60%, or at least 70% in the level of LHC transcripts compared to the control cell or organism.

The structure of a gene consists of many elements, of which the protein coding sequence is only one part. The gene includes nucleic acid sequences that are not transcribed and sequences that are untranslated regions of the RNA. Genes also contain regulatory sequences, which includes promoters, terminators, enhancers, silencers, introns, 3' and 5' UTRs, and coding sequences, as well as other sequences known to be a part of genes. In various embodiments any of these structures or nucleic acid sequences (e.g. any of SEQ ID NO: 14-26 or variants of any) can have one or more of the genetic modifications described herein that result in the higher lipid productivity and/or higher biomass productivity as described herein.

WD40 Repeat Containing Protein

WD40 repeat containing proteins (or domains) have four or more repeating units containing a conserved core motif that ends with tryptophan-aspartic acid (WD). Proteins of this class have domain folds that form a beta propeller structure, which are symmetric folds having 4-9 anti-parallel, four-stranded beta sheets arranged radially around a central axis. The domains form a platform on which protein complexes assembly reversibly. They are believed to play a key role in the formation of protein-protein complexes. In any embodiment the genetic modification to the WD40 repeat containing protein can be to any WD40 repeat domain of the protein.

The recombinant algal cell or organism of the invention can have a genetic modification described herein to a nucleic acid sequence of any of SEQ ID NO: 14-26, or to a nucleic acid sequence having at least 60% sequence identity or at least 70% sequence identity or at least 75% or at least 80% or at least 85% or at least 90% or at least 95% or at least 98% sequence identity to any of SEQ ID NOS: 14-26. The nucleic acid sequence can encode a WD40 repeat containing protein. The genetic modification can also be to any of the disclosed sequences and also have at least 500 or at least 600 or at least 700 or at least 800 or at least 1000 or at least 1200 or at least 1400 or at least 1500 contiguous nucleotides of any sequence of SEQ ID NO: 14-26 (and, optionally, also have a recited percent identity).

The genetic modification can be to a gene or nucleic acid sequence that encodes a WD40 repeat containing protein having a polypeptide sequence of any one of SEQ ID NO: 1-13 or a variant of any of said nucleic acid sequences, and the genetic modification can result in the higher lipid productivity and/or higher biomass productivity as described herein. In various embodiments the genetic modification can be to a nucleic acid sequence that encodes a WD40 repeat containing protein (or domain) having at least 60% sequence identity or at least 70% sequence identity or at least 75% or at least 80% or at least 85% or at least 90% or at least 95% or at least 98% sequence identity to any of SEQ ID NOS: 1-13. In some embodiments the nucleic acid sequence can be a variant as stated and also encode at least 25 or at least 50 or at least 75 or at least 100 or at least 150 or at least 200 or at least 250 or at least 300 or at least 350 or at least 400 contiguous amino acids of any one of SEQ ID NOs: 1-13, or a variant of any.

In any embodiment the WD40 repeat containing protein can be a functional WD40 repeat containing protein. In various embodiments the recombinant algal cell or organism can have a genetic modification described herein to a nucleic acid sequence of SEQ ID NO: 15 or 16, or to a variant of either having at least 70%, or at least 75%, or at least 80%, or at least 85%, or at least 90%, or at least 95%, or at least 98% sequence identity.

Persons of ordinary skill know how to calculate the percent of "sequence identity" between two sequences. Any method of determining sequence identity that has acceptance by most persons of ordinary skill in the art or otherwise widely accepted in the field can be utilized to determine the sequence identity between two sequences. In one embodiment the percent of sequence identity can be determined by BLAST (Basic Local Alignment Search Tool) analysis using the algorithm employed by the programs blastp, blastn, blastx, tblastn, and tblastx (Altschul (1997), Nucleic Acids Res. 25, 3389-3402, and Karlin (1990), Proc. Natl. Acad. Sci. USA 87, 2264-2268). In one embodiment the search parameters for histogram, descriptions, alignments, expect (i.e., the statistical significance threshold for reporting matches against database sequences), cutoff, matrix, and filter (low complexity) can be at the default settings. The default scoring matrix used by blastp, blastx, tblastn, and tblastx can be the BLOSUM62 matrix (Henikoff (1992), Proc. Natl. Acad. Sci. USA 89, 10915-10919). For blastn the scoring matrix can be set by the ratios of M (i.e., the reward score for a pair of matching residues) to N (i.e., the penalty score for mismatching residues), wherein the default values for M and N can be +5 and −4, respectively. Four blastn parameters can be adjusted as follows: Q=10 (gap creation penalty); R=10 (gap extension penalty); wink=1 (generates word hits at every winkth position along the query); and gapw=16 (sets the window width within which gapped alignments are generated). The equivalent Blastp parameter settings for comparison of amino acid sequences can be: Q=9; R=2; wink=1; and gapw=32. A Bestfit comparison between sequences, available in the GCG package version 10.0, can use DNA parameters GAP=50 (gap creation penalty) and LEN=3 (gap extension penalty), and the equivalent settings in protein comparisons can be GAP=8 and LEN=2.

Laboratory Strains

In various embodiments the one or more genetic modification(s) can be made in (i.e. derived from) a cell or organism that is a wild type, parent, or laboratory strain. Laboratory strains are cells or organisms that have been cultured in a laboratory setting. As a result of culturing over a period of time the strain has undergone some adaptation(s) advantageous to growth in the laboratory setting. A laboratory strain therefore can develop one or more advantageous characteristics from adaptations deriving from time of culturing in the laboratory environment. For example, laboratory strains can have higher biomass productivity and/or higher lipid productivity than a wild-type strain. In some embodiments one or more genetic modifications disclosed herein can be performed on a laboratory strain to result in a recombinant algal cell or organism of the invention. In such embodiments the laboratory strain can therefore be a corresponding control algal cell or organism described herein that does not have the genetic modification being considered. A test cell can be derived from the corresponding control cell or organism. For example, the corresponding control cell or organism can be a parental strain of the test cell or organism.

Increased Lipid Productivity

The recombinant mutant algae of the invention having a genetic modification to a gene or nucleic acid sequence encoding a WD40 repeat containing protein or other modification described herein can demonstrate an increase in the production of lipid in the cell or organism versus a corresponding (control) cell or organism. The increase in lipid production can be measured by any accepted and suitable method, for example using fatty acid methyl ester (FAME) analysis. In one embodiment the increase in lipid production is measured as an increase in total FAME produced by the recombinant organisms. The recombinant cells or organisms of the invention have a genetic modification to a gene or nucleic acid sequence encoding a WD repeat containing protein or domain and can exhibit at least 20% or at least 25% or at least 30% or at least 40% or at least 50% or at least 60% or at least 70% or at least 80% or at least 90% or at least 100% greater lipid productivity compared to a corresponding control cell or organism, as described herein. In other embodiments the increase in lipid productivity can be 15-25% or 15-35% or 15-45% or 15-50% or 20-25%, or 25-45%, or 25-55%, or 25-70%, or 25-90%, or 25-100%, or 25-150% or 25-200% or 30-35% or 30-45% or 30-55%. The increase can be weight for weight (w/w) of lipid. In any embodiment the lipid can be fatty acid. In one embodiment lipid productivity is measured using the FAME profile (fatty acid methyl ester) of the respective cells or organisms. In one embodiment lipid productivity can be expressed as mg/L. In other embodiments the recombinant cells or organisms of the invention can exhibit at least 50 g/m2 or at least 60 or at least 70 or at least 80 grams per square meter of FAME accumulation after 5 days of cultivation. Methods of producing a FAME profile are known to persons of ordinary skill in the art. A FAME profile can be determined using any suitable and accepted method, for example a method accepted by most persons of ordinary skill in the art. The recombinant cell or organisms of the invention can, optionally, also have an increase in biomass productivity can be 15-35% or 15-40% or 25-45% or 15-50% or 25-70% or 50-100% or 50-200% (w/w).

An increase in lipid production or lipid productivity can be measured by weight, but can also be measured in grams per square meter per day of the surface of a cultivation vessel (e.g. a flask, photobioreactor, cultivation pond). In various embodiments the recombinant cell or alga of the invention produces at least 3 or at least 4 or at least 5 or at least 6 or at least 7 or at least 8 or at least 10 or at least 12 or at least 13 or at least 14 grams per square meter per day of lipid production, which can be measured by the FAME profile. In any of the embodiments the high lipid and/or high biomass productivity phenotype can be obtained under nitrogen deplete conditions, which in some embodiments can involve dilution and/or replacement of medium with fresh nitrogen deplete medium during growth. Dilutions can be by any suitable amount, for example dilution by about 50% or by about 60% or by about 70% or at least 70%, or by about 80%, or by more than 80%, which can be done every day, every 2 days, every 3 days or every 4 days or every 5 days. In one embodiment the lipid product is a fatty acid and/or a derivative of a fatty acid. In one embodiment the fatty acids and/or derivatives of fatty acid comprise one or more species of molecules having a carbon chain between C8-C12, and/or C8-C18 and/or C8-C20 and/or C8-C22 and/or C8-C24, hereby disclosed in all possible combinations and sub-combinations. In one embodiment the growth conditions can be batch growth, involving spinning cells to remove nitrogen from the medium, replacing with nitrogen deplete medium, and resuming batch growth.

In any of the embodiments the genetic modification to the gene or nucleic acid sequence encoding a WD repeat containing protein can result in an attenuation of expression of the respective genes. The genetic modification of any one or more of these genes or nucleic acids can be any of those described herein, e.g. any one or more of SEQ ID NOs: 14-26. In one embodiment the genetic modification is a deletion, disruption, or inactivation. In another embodiment the genetic modification is a deletion (which optionally, can be a functional deletion) or a disruption of the gene.

Biomass Productivity

The recombinant algal cells of the invention having a genetic modification to a gene or nucleic acid sequence encoding a WD40 repeat containing protein described herein, and can also have higher biomass productivity than a corresponding (control) organism not having the genetic modification. Biomass can be measured as an increase in the total organic carbon (TOC) produced by the cell or organism, for example measured by TOC analysis known to persons of ordinary skill in the art. The recombinant cells can have at least 12% higher, or at least 15% higher, or at least 20% higher or at least 25% higher or at least 30% higher or at least 35% higher, or at least 50% higher or at least 60% higher or at least 70% higher or at least 80% higher or at least 90% higher or at least 100% higher or at least 125% higher or at least 150% higher biomass productivity than a corresponding (control) cell or organism, which can be measured by total organic carbon analysis. In other embodiments the biomass productivity can be 10-15% higher or 15-25% higher or 20-25% higher or 20-30% higher or 20-40% higher or 20-45% higher. The increase in biomass productivity can, optionally, be in addition to the increase in lipid productivity.

Various methods of measuring total organic carbon are known to persons of ordinary skill in the art. Biomass productivity can be measured as mg/ml of culture per time period (e.g. 1 day or 2 days or 3 days or 4 days or 5 days). In some embodiments the higher biomass productivity and/or higher lipid productivity as described herein can occur under nitrogen deplete conditions. Thus, in one embodiment the recombinant alga or cell of the invention can have higher lipid production and/or higher total organic carbon production than a corresponding (control) cell or organism, which higher amount can be produced under nitrogen deplete or low nitrogen conditions. Nitrogen deplete conditions can involve culturing in a buffer having less than 0.5 mM of nitrogen in any available form external to the cell or organism. In some embodiments the cells can be cultured in 0.5 mM or less of KNO3 or urea as a nitrogen source. Other buffers may also be used and be nitrogen deplete [[if they contain a level of nitrogen that does not change the physiology of a nitrogen-related parameter (e.g. lipid productivity or biomass productivity) by more than 10% versus culturing the cell in a medium free of a nitrogen source external to the cells or organisms.]] In any embodiment biomass productivity can be evaluated by measuring an increase in the total organic carbon of the cells. Nutrient replete conditions are those where the growth of the cultivated organism is not limited by a lack of any nutrient. A nitrogen free medium is also considered nitrogen deplete conditions.

Methods of Producing Lipid

The invention also provides methods for producing a lipid containing product. The methods involve culturing a recombinant algal cell or organism described herein to thereby produce a lipid product. Any of the methods can also involve a step of harvesting lipid produced by the recombinant algal cell or organism described herein. The culturing can be for a suitable period of time, for example, at least 1 day or at least 3 days or at least 5 days.

The invention also provides methods for producing a composition containing lipids. In one embodiment the methods can involve performing a genetic modification to an algal organism in a gene or nucleic acid sequence encoding a WD40 repeat containing protein. The methods can also involve a step of culturing a recombinant algal cell or organism described herein to thereby produce a composition containing lipids. The composition can be a biomass composition or biomass product containing any one or more recombinant algae described herein. The cultivating can be done in any suitable medium conducive to algal growth (e.g. an algal growth medium or any medium described herein). The methods can also involve a step of harvesting lipids from the composition or biomass containing lipids. The methods can involve a step of harvesting lipids from the recombinant cells or organisms. Any of the methods herein can also involve a step of purifying the lipid containing composition to produce a biofuel or biofuel precursor. A biofuel precursor is a composition containing lipid molecules that can be purified or otherwise converted into a biofuel.

The invention also provides methods of producing a recombinant algal cell or organism having higher lipid productivity and/or higher biomass productivity than a corresponding control cell or organism. The methods involve exposing algal cells or organisms to ultraviolet light to produce a recombinant cell or organism described herein that has higher lipid productivity than a corresponding control cell or organism. In one embodiment algal organisms having higher lipid productivity can be identified by contacting the recombinant cells with a stain that identifies lipids (e.g. by BODIPY dye). Optionally methods can include a step of isolating lipids from the recombinant algal organisms. Organisms having higher biomass productivity can be identified by TOC analysis. The recombinant alga can be cultivated in any suitable growth media for algae, such as any of those described herein. The uv treatment can involve, for example, subjecting the culture to uv light, or gamma radiation, or both, for a suitable period of time or under a suitable uv regimen or gamma radiation regimen. Persons of ordinary skill understand suitable regimens for uv exposure for mutagenesis. The uv regimen can involve exposing the cells or organisms to uv radiation, which can be performed in batches with each batch receiving a dose. Multiple cell batches can receive different doses of energy for each batch of cells. Subjecting the algal organism to ultra-violet light can comprise exposing the cell or organism to at least 10 or at least 15 uJ/cm2 of energy, which exposure can be performed within 1 second or within 5 seconds or within 30 seconds or within 1 minute. In some embodiments 4 or 5 batches of cells can receive doses of exposure to 16-57 uJ/cm2 of energy, and exposure energy can increase with each separate batch. The cell batches can be pooled together after exposures are complete. The recombinant alga (or pooled algae) can be cultivated for at least 2 days or at least 3 days, or at least 4 days, or at least 5 days, or at least 6 days, or at least 10 days, or at least 20 days, or from 2-10 days, or from 2-20 days or from 2-25 days after exposure. The recombinant algal organisms can be any described herein. The uv regimen can involve exposing the cells or organisms to multiple exposures to uv radiation, which can become progressively stronger.

Any of the recombinant cells or organisms of the invention can be cultivated in batch, semi-continuous, or continuous culture to produce the higher biomass productivity and/or higher lipid productivity. In some embodiments the culture medium can be nutrient replete, or nitrogen deplete (—N). In some embodiment the culturing is under photoautotrophic conditions, and under these conditions inorganic carbon (e.g., carbon dioxide or carbonate) can be the sole or substantially the sole carbon source in the culture medium.

The invention also provides a biofuel comprising a lipid product of any of the recombinant cells or organisms described herein. The biofuel is produced by purifying a lipid containing composition produced by a recombinant algal cell or organism described herein. The biofuel can be produced by purifying or otherwise converting a lipid product produced by a recombinant algal cell or organism described herein to produce a biofuel. In one embodiment the biofuel is a biodiesel fuel, which can contain fatty acid methyl ester molecules in sufficient proportion to be combustible in an internal combustion engine. In various embodiments the biofuel can contain carbon chains with an average carbon chain length of at least 5 carbon atoms, or at least 8 carbon atoms, or at least 10 carbon atoms.

FAME and TOC Analysis Methods

The lipid productivity of the cells or organisms can be measured by any method accepted in the art, for example as an increase or decrease in fatty acid methyl esters comprised in the cell, i.e. FAME analysis. In various embodiments any of the recombinant algal cells or organisms of the invention can have higher biomass productivity as described herein versus corresponding control cells or organisms. In some embodiments the recombinant algal cells or organisms of the invention can have higher lipid productivity and also higher biomass productivity compared to a corresponding control cell or organism. Biomass productivity can be measured by any methods accepted in the art, for example by measuring the total organic carbon (TOC) content of a cell. Embodiments of both methods are provided in the Examples.

"FAME lipids" or "FAME" refers to lipids having acyl moieties that can be derivatized to fatty acid methyl esters, such as, for example, monoacylglycerides, diacylglycerides, triacylglycerides, wax esters, and membrane lipids such as phospholipids, galactolipids, etc. In some embodiments lipid productivity is assessed as FAME productivity in milligrams per liter (mg/L), and for algae, may be reported as grams per square meter per day (g/m2/day). In semi-continuous assays, mg/L values are converted to g/m2/day by taking into account the area of incident irradiance (the SCPA flask rack aperture of 1½ inches×3⅜", or 0.003145 m2) and the volume of the culture (550 ml). To obtain productivity values in g/m2/day, mg/L values are multiplied by the daily dilution rate (30%) and a conversion factor of 0.175. Where lipid or subcategories thereof (for example, TAG or FAME) are referred to as a percentage, the percentage is a weight percent unless indicated otherwise. The term "fatty acid product" includes free fatty acids, mono-di, or tri-glycerides, fatty aldehydes, fatty alcohols, fatty acid esters (including, but not limited to, wax esters); and hydrocarbons, including, but not limited to, alkanes and alkenes).

Embodiments

In one embodiment the invention provides a recombinant algal organism of the Class Trebouxiophyceae having a genetic modification in a gene or nucleic acid sequence encoding a WD40 repeat containing protein. The recombinant alga exhibits higher lipid productivity and/or biomass productivity versus a corresponding control algal cell not having the genetic modification. In various embodiment the Trebouxiophyceae organism can be from the family Oocystaceae or Chlorellaceae. In one embodiment the organism is of the genus *Oocystis*.

In one embodiment the invention provides a recombinant Trebouxiophyceae organism having a deletion, disruption, or inactivation in a gene or nucleic acid sequence encoding a WD40 repeat containing protein. The deletion can be a functional deletion. In one embodiment the deletion, disruption, or inactivation involves the insertion of a nonsense mutation or a frameshift mutation in a gene or nucleic acid sequence encoding a WD40 repeat containing protein. In one embodiment the encoded WD40 repeat containing protein can have at least 80% or at least 85% or at least 90% or at least 95% sequence identity to SEQ ID NO: 1 or 8. In another embodiment the recombinant cell or organism can have the deletion, disruption, or inactivation in a nucleic acid sequence encoding a WD40 repeat containing protein, which be a nucleic acid having at least 80% or at least 90% or at least 95% sequence identity to SEQ ID NO: 15 or SEQ ID NO: 16. The recombinant alga exhibits higher lipid productivity and/or biomass productivity versus a corresponding control algal cell not having the genetic modification. The alga can be a Trebouxiophyceae organism, for example from the family Oocystaceae, and optionally from the genus *Oocystis*. The increase in lipid productivity can be an increase in 2-day FAME accumulation of at least 20% w/w, or at least 25%, or 30-50% or 30-55%, which can, optionally, be cultivated under nitrogen deplete conditions. The recombinant cells or organisms can, optionally, also have an increase in biomass productivity of at least 12% or at least 15% or at least 20% or 15-25% or 20-40%, which can be expressed as 2-day TOC accumulation. Thus in one embodiment the recombinant cells or organisms have an increase in lipid productivity (as measured by FAME profile) of 30-55% and an increase in biomass productivity of at least 20% versus a control cell or organism. In another embodiment the increase in lipid productivity can be 20-40%. The increase in FAME accumulation and/or TOC accumulation can be measured after two days or after five days cultivation, and can be in nitrogen deplete conditions. The recombinant cells or organisms can also have a FAME/TOC ratio of greater than 0.3 after 2 days of cultivation.

In another embodiment the cells or organisms of the invention can have an increase in lipid productivity of at least 20% (as measured by 2-day FAME accumulation) and, optionally, an increase in biomass productivity of at least 12% (as measured by TOC); and optionally also have a FAME/TOC ratio of greater than 0.3 or 0.4. In another embodiment the cells or organisms of the invention can have an increase in lipid productivity of at least 20% (as measured by 2-day FAME accumulation); and optionally also have a FAME/TOC ratio of greater than 0.5.

In one embodiment the invention provides a recombinant algal organism of the Class Trebouxiophyceae having a genetic modification to a gene or nucleic acid sequence encoding a WD40 repeat containing protein. In one embodiment the gene or nucleic acid sequence is any one of SEQ ID NO: 14-26 or a variant of any, or can be a gene or nucleic acid sequence encoding any one of SEQ ID NO: 1-13, or a variant of any. The genetic modification can be a deletion (optionally a functional deletion) or disruption of the gene or nucleic acid sequence. The deletion can be a functional deletion. The recombinant alga exhibits higher lipid productivity and, optionally, higher biomass productivity versus a corresponding control algal cell not having the genetic modification. In various embodiment the Trebouxiophyceae organism can be from the family Oocystaceae or Chlorellaceae. In one embodiment the organism is of the genus *Oocystis*. The increase in lipid productivity can be an increase in 2-day or 5-day FAME accumulation of at least 20% w/w, or 30-50% or 30-55%, which can, optionally, be cultivated under nitrogen deplete conditions. The recombinant cells or organisms can, optionally, also have an increase in biomass productivity of at least 15% or at least 20% or 15-25% or 20-40%, which can be expressed as 2-day or 5-day TOC accumulation. Thus in one embodiment the recombinant cells or organisms have an increase in lipid productivity of 30-55% and an increase in biomass productivity of at least 20%. In another embodiment the increase in lipid productivity can be 20-40%. The increase in FAME accumulation and/or TOC accumulation can be measured after two days or after five days cultivation in nitrogen deplete conditions. In another embodiment the cells or organisms of the invention can have an increase in lipid productivity of at least 50% (as measured by 5-day FAME accumulation); and optionally also have a FAME/TOC ratio of greater than 0.5 or 0.6 after 5 days cultivation.

In all embodiments the increase in lipid productivity and/or TOC productivity can be relative to a corresponding (control) cell or organism, which can be a wild-type cell or a laboratory strain.

Example 1

Various aliquots of 10 mL of Strain 15 (STR00015 or "wild type") *Oocystis* sp. were acclimated to diel growth conditions on urea supplemented minimal media. Different aliquots of cells at a concentration of 2×10$^6$ cells/mL were then exposed to different amounts of UV radiation (22.4, 33.6, 44.8 and 56 mJ/cm² using at total of 50, 50, 50 and 20 mL of culture, respectively) in a UV crosslinker apparatus. The mutagenized cell aliquots were allowed to recover in the dark for 48 hrs. Cultures were then scaled up in low light (~100uE) before a first round of enrichment. The mutagenized cells were then acclimated to diel growth at a light intensity of ~100 uE and 1% $CO_2$ in urea supplemented minimal medium for a week. The cultures were scaled up for 3 days, bubbled with 1% $CO_2$ at a maximum irradiance of 1400 uE under diel conditions, to an OD730 of about 1.0. The cultures was then centrifuged at 5000 g for 10 mins and the cell pellets resuspended in nitrogen-free minimal medium to an OD730 of about 0.9. This nitrogen-free culture was then incubated for 48 hrs in square-bottom flasks bubbled with 1% $CO_2$ at a maximum irradiance of about 1400 uE under diel conditions. After 48 hours in nitrogen-free batch growth, an aliquot of cells was removed and subjected to staining with the lipid specific dye BODIPY for 10 mins in the dark at a final concentration of 0.2 ug/mL.

Mutant cells having the highest level of BODIPY staining were enriched by fluorescence activated cell sorting (FACS). Enriched cell populations were scaled up and starved for nitrogen as described above, and then subjected to additional rounds of BODIPY-based FACS enrichment. This iterative process was repeated for a total of five rounds, with the top 2%, 1%, 1%, 0.25% and 0.25% of the population retained in each iteration.

The final sort was plated on minimal medium agar plates supplemented with urea to isolate single axenic colonies.

Isolates were scaled up in T25 tissue culture flasks in minimal medium supplemented with urea, then transitioned to nitrogen-free minimal medium for 48 hrs. The lipid and biomass accumulation of isolated mutants were compared to the parental strain STR00015, with lipid content measured by total fatty acid methyl ester (FAME) analysis and biomass measured by total organic carbon (TOC). As can be seen in FIG. 1, several isolates from the screen showed an increase in accumulated FAME and TOC, as well as FAME/TOC—an indicator of how much fixed carbon is partitioned to lipids. This indicated that mutants with improved lipid productivity had been isolated by the process described. Strain 27434 was identified as having high FAME and biomass accumulation.

Example 2

Genomic DNA was isolated from Strain 27434 along with parental (wild type) Strain 15 and sequenced on high throughput sequencing system generating 150 bp paired end reads. Reads were processed, mapped to the wild type strain as reference genome and analyzed by a small variants algorithm. An example of a small variants algorithm is the Freebayes polymorphism detection software, although other programs can also be successfully utilized. Analysis of SNPs and small insertions/deletions (InDels) revealed Strain '434 contained a total of 170 polymorphisms. Twenty-four of these mutations were located within exons or at splice junctions and were prioritized for Cas9-mediated gene deletion as they had the highest probability of altering gene function and/or activity, as shown in Table 1 below.

TABLE 1

Mutations identified within exons or at splice junctions in Strain '434

| | Transcripts | Descriptions | Type | Ref | Alt | AAMod |
|---|---|---|---|---|---|---|
| 1 | 3EUKT2015873 | Protein kinase-like (PK-like) | SNP | G | A | Gln1301* |
| 2 | 3EUKT2027500 | YVTN repeat-like/Quinoprotein amine dehydrogenase | Deletion | AGACTCGCACCG | AG | Val204fs |
| 3 | 3EUKT2031181 | CAAX amino terminal protease self-immunity | SNP | G | A | Gln48* |
| 4 | 3EUKT2028953 | Proteasome subunit alpha type-1-A | SNP | C | T | Leu546Phe |
| 5 | 3EUKT2014620 | 3-methylcrotonyl-CoA carboxylase alpha subunit | SNP | C | A | Ala426Ser |
| 6 | 3EUKT2012690 | DNA-directed DNA polymerase family protein | SNP | G | A | Ala627Val |
| 7 | 3EUKT2036647 | Conserved predicted protein | SNP | C | T | Glu640Lys |
| 8 | 3EUKT2016841 | Conserved predicted protein | SNP | T | A | Leu332Gln |
| 9 | 3EUKT2025932 | Chitin binding Peritrophin-A domain | SNP | C | T | Pro239Leu |
| 10 | 3EUKT3238737 | Retrovirus-related Pol polyprotein from transposon 17.6 | SNP | G | A | Ser895Phe |
| 11 | 3EUKT2017815 | Phosphoglycerate mutase-like protein | Complex | CC | TT | Gly235Glu |
| 12 | 3EUKT2020372 | Conserved predicted protein | SNP | A | G | Thr118Ala |
| 13 | 3EUKT2011248 | RAP domain | SNP | G | A | Gly1722Asp |
| 14 | 3EUKT2015114 | Conserved predicted protein | SNP | G | A | Arg576His |
| 15 | 3EUKT2013326 | Manganese-dependent ADP-ribose/CDP-alcohol diphosphatase | SNP | G | A | Ser174Phe |
| 16 | 3EUKT2015233 | Phosphatidylinositol (PI) phosphodiesterase | SNP | C | T | Ser106Phe |
| 17 | 3EUKT2015577 | T-complex 1 subunit beta | SNP | G | A | Glu265Lys |
| 18 | 3EUKT2015261 | Cell surface protein homologous to bacterial outer membrane proteins | SNP | C | T | Pro171Ser |
| 19 | 3EUKT2026772 | Conserved predicted protein | SNP | G | A | Pro18Ser |
| 20 | 3EUKT2021194 | Conserved predicted protein | SNP | C | T | Pro48Leu |
| 21 | 3EUKT2021524 | Conserved predicted protein | SNP | C | T | Ser19Leu |
| 22 | 3EUKT2018868 | Conserved predicted protein | SNP | T | A | Asn84Ile |
| 23 | 3EUKT2022105 | Axonemal inner arm dynein heavy chain 4 | SNP | G | A | Ala202Val |
| 24 | 3EUKT2018529 | Ribonuclease Inhibitor | SNP | G | A | Splice junction |

The remaining 146 mutations were either intergenic or present in introns of a gene. An assessment of transcriptomics data from Strain 15 (wt) and Strain 27434 indicated that none of these 146 mutations had any significant impact on gene expression or transcript splicing.

Example 3—Identification of Mutations

To identify which mutation(s) caused the high lipid phenotype in Strain 27434, independent knockouts of genes bearing SNPs in the strain (Table 1) were conducted via RNP-based Cas9-mediated gene disruption in two background strains: (i) the Strain 15 wild type parental strain; and (ii) Strain 24194—a laboratory strain evolved from Strain 15 and having improved biomass and lipid productivity.

All the strains generated were tested for improved biomass and lipid accumulation during nitrogen starvation in T25 flasks. From this analysis three independent lines were identified having a deletion of 3EUKT2027500, a gene encoding a WD40 repeat containing protein. These lines showed significantly higher biomass and lipid accumulation compared to the parental lines. One of these was constructed in the Strain 15 (wt) control strain (FIG. 2), while the other two were constructed in the Strain 24194 control strain (FIG. 3). As shown in FIG. 2, the first genetically engineered strain (identified as Strain 29857) showed a 22% and 15% improvement in accumulated FAME and TOC, respectively, compared to Strain 15. The strains engineered in the Strain 24194 control (identified as Strains 30525 and 30526) showed a 22% increase in FAME accumulation (FIG. 3).

Example 4

Large scale productivity testing in 500 mL square-bottom flasks was conducted as described above, but over a 5 day period. The study revealed that the two knockout lines in laboratory Strain 24194 (Strain 30525 and 30526) showed a 14% and 21% improvement in lipid productivity, respectively (FIG. 4), confirming the results in the T25 flasks. The measured FAME/TOC was also substantially higher on each day of the experiment for both engineered strains (FIG. 4). The data therefore showed that deletion of 3EUKT2027500 provides a substantial increase in carbon partitioning and lipid productivity.

Example 5

The amino acid sequence of 3EUKT2027500 (#2 in Table 1) was analyzed for functional domains and orthologs in other species. 3EUKT2027500 encodes a WD40 repeat containing protein with four tandem domains with weak similarity to WD40 repeats. WD40 repeats are short minimally conserved structural motifs of about 40 amino acids often beginning with a glycine-histidine (GH) dipeptide and ending with tryptophan-aspartic acid (WD) dipeptide. Multiple copies of these repeats fold together to form the WD40 domain, which functions as a scaffold enabling interaction with proteins and nucleic acid and facilitating the formation of multiprotein complexes. WD40 repeat containing proteins are involved in a variety of cellular processes, including cell cycle progression, transcriptional regulation, signal transduction, apoptosis, biosynthesis of plant cell walls, anthocyanin biosynthesis, etc.

Further sequence identity analysis summarized in Table 2 revealed orthologs of 3EUKT2027500 are highly conserved and broadly distributed in green algae and plants.

TABLE 2

Alignment of entire protein sequences of 3EUKT2027500 orthologs

| | Organisms | Gene/Seq ID | % Identity | % Similarity [Positives] |
|---|---|---|---|---|
| 1 | Coccomyxa subellipsoidea | XP_005642574.1 SEQ ID NO: 2 | 78 | 89 |
| 2 | Chlamydomonas reinhardtii | Cre16.g674000 SEQ ID NO: 3 | 69 | 78 |
| 3 | Volvox carteri | XP_002950453.1 SEQ ID NO: 4 | 72 | 80 |
| 4 | Auxenochlorella protothecoides | RMZ56784.1 SEQ ID NO: 5 | 62 | 76 |
| 5 | Chlorella sorokiniana | PRW57951.1 SEQ ID NO: 6 | 70 | 81 |
| 6 | Chlorella variabilis | XP_005847572.1 SEQ ID NO: 7 | 69 | 80 |
| 7 | Parachlorella sp WT1185 | 3EUKT595038 SEQ ID NO: 8 | 73 | 85 |
| 8 | Picochlorum celeri | 3EUKT2133049 SEQ ID NO: 9 | 44 | 62 |
| 9 | Tetraselmis | 3EUKT668672 SEQ ID NO: 10 | 73 | 82 |
| 10 | Ostreococcus lucimarinus | XP_001417471.1 SEQ ID NO: 11 | 71 | 86 |
| 11 | Micromonas commoda | XP_002507884.1 SEQ ID NO: 12 | 72 | 87 |
| 12 | Arabidopsis | AT1G12910 SEQ ID NO: 13 | 70 | 83 |

An alignment study of the protein sequences from the Table 2 orthologs was conducted and showed a high degree of sequence conservation across Chlorophyte algae species and across the entire length of the proteins, and particularly in key domains as illustrated in FIG. 5. Sequence similarity was calculated using the bioinformatics matrix BLOSUM62 for sequence alignment.

It will be readily apparent to one skilled in the art that varying substitutions and modifications may be made to the invention disclosed herein without departing from the scope and spirit of the invention.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described. Other embodiments are within the following claims.

What is claimed:

1. A recombinant algal organism comprising a deletion, disruption, or inactivation of a gene or nucleic acid sequence encoding a WD40 repeat containing protein having at least 90% sequence identity to SEQ ID NO: 1, wherein the recombinant alga has higher lipid productivity and/or higher biomass productivity versus a corresponding control algal cell not having the genetic modification.

2. The recombinant alga of claim 1, wherein the recombinant alga is a Chlorophyte alga.

3. The recombinant alga of claim 2, wherein the alga is of the Class Trebouxiophyceae.

4. The recombinant algal of claim 3, wherein the gene or nucleic acid sequence encoding a WD40 repeat containing protein comprises a nucleic acid sequence having at least 90% sequence identity to a nucleic acid sequence of SEQ ID NO: 15 or SEQ ID NO: 16.

5. The recombinant alga of claim 3, wherein the deletion, disruption or inactivation of the gene encoding the WD40 repeat containing protein is a knock out mutation.

6. The recombinant alga of claim 3, wherein the deletion, disruption, or inactivation of the gene encoding the WD40 repeat containing protein results in an attenuation in the expression of the nucleic acid sequence.

7. The recombinant alga of claim 3, wherein the deletion, disruption, or inactivation of the gene encoding the WD40 repeat containing protein comprises the deletion of one or more amino acids in a polypeptide sequence of a WD40 repeat containing protein.

8. The recombinant alga of claim 3, wherein the deletion, disruption, or inactivation of the gene encoding the WD repeat containing protein comprises a frame shift mutation.

9. The recombinant alga of claim 1, wherein the recombinant alga has at least 30% higher lipid productivity versus a corresponding control alga that does not comprise the genetic modification.

10. The recombinant alga of claim 9, wherein the recombinant alga has at least 15% higher biomass productivity as measured by total organic carbon versus a control alga that does not comprise the genetic modification.

11. The recombinant alga of claim 1, wherein the recombinant alga exhibits at least 40 grams per square meter per day of lipid production after 5 days of cultivation.

12. The recombinant alga of claim 1, wherein the recombinant alga has higher biomass productivity per unit time as measured by production of total organic carbon (TOC).

13. The recombinant alga of claim 12, wherein the recombinant alga has higher biomass productivity under nitrogen deficient conditions.

14. The recombinant alga of claim 1, wherein the recombinant alga has higher total organic carbon production under nitrogen deficient conditions.

15. The recombinant alga of claim 3, wherein the recombinant alga is of a family selected from the group consisting of: Oocystaceae, Chlorellaceae, and Eustigmatophyceae.

16. The recombinant alga of claim 3, wherein the recombinant alga is of a genus selected from the group consisting of: *Chlorella, Parachlorella, Picochlorum, Tetraselmis*, and *Oocystis*.

17. The recombinant alga of claim 16, wherein the recombinant alga is an alga of the genus *Oocystis*.

18. A biomass product comprising the recombinant alga of claim 1.

\* \* \* \* \*

SEQUENCE LISTING

```
<160> NUMBER OF SEQ ID NOS: 26

<210> SEQ ID NO 1
<211> LENGTH: 340
<212> TYPE: PRT
<213> ORGANISM: Oocystis sp.
<220> FEATURE:
<221> NAME/KEY: misc_feature
<223> OTHER INFORMATION: WD40 repeat protein, 3EUKT2027500

<400> SEQUENCE: 1

Met Ala Glu Pro Asp Ala Asn Gly Ala Ser Asp Gly Lys Arg Ala Glu
1               5                   10                  15

Ile Tyr Thr Tyr Glu Phe Pro Asn Leu Val Tyr Ser Met Asn Trp Thr
            20                  25                  30

Ser Arg Arg Asp Lys Lys Phe Arg Leu Ala Val Gly Ser Phe Ile Glu
        35                  40                  45

Asp Tyr Asn Asn Val Val Asn Ile Ile Ser Leu Asp Glu Glu Gln Gly
    50                  55                  60

Lys Phe Val Cys Asp Pro Ser Leu Thr Phe Lys His Pro Tyr Pro Pro
65                  70                  75                  80

Thr Lys Val Met Phe Val Pro Asp Arg Glu Gly Thr Arg Pro Asp Leu
                85                  90                  95

Leu Ala Thr Thr Gly Asp Tyr Leu Arg Val Trp Lys Ile Gly Glu Asp
            100                 105                 110

Gly Val Thr Leu Gln Lys Leu Leu Asn Asp Asn Lys Asn Ser Glu Phe
        115                 120                 125

Cys Ala Pro Leu Thr Ser Phe Asp Trp Asn Glu Thr Asp Pro Lys Arg
    130                 135                 140

Leu Gly Thr Ser Ser Ile Asp Thr Thr Cys Thr Ile Trp Asp Ile Glu
145                 150                 155                 160

Lys Gly Val Val Asp Thr Gln Leu Ile Ala His Asp Lys Glu Val Tyr
                165                 170                 175

Asp Ile Ala Trp Gly Gly Val Gly Val Phe Ala Ser Val Ser Ala Asp
            180                 185                 190

Gly Ser Val Arg Val Phe Asp Leu Arg Asp Lys Glu His Ser Thr Ile
        195                 200                 205

Ile Tyr Glu Thr Pro Ser Pro Glu Thr Pro Leu Leu Arg Leu Gly Trp
    210                 215                 220

Asn Lys Gln Asp Pro Arg Tyr Met Ala Thr Ile Val Met Asp Ser Asn
225                 230                 235                 240

Arg Val Val Val Leu Asp Ile Arg Val Pro Thr Val Pro Val Ala Glu
                245                 250                 255

Leu Gln Arg His Gln Ala Cys Ala Asn Ala Leu Ala Trp Ala Pro His
            260                 265                 270

Ser Ser Cys His Ile Cys Thr Ala Gly Asp Asp Ala Gln Ala Leu Ile
        275                 280                 285
```

```
Trp Asp Leu Ser Ala Val Ser Lys Glu Gly Asp Ser Gly Leu Asp Pro
        290                 295                 300

Ile Leu Ala Tyr Asn Ala Gly Gln Glu Val Asn Gln Leu Gln Trp Ser
305                 310                 315                 320

Ser Thr Gln Pro Asp Trp Val Ala Val Cys Phe Gly Asn Lys Ala Gln
                325                 330                 335

Ile Leu Arg Val
            340

<210> SEQ ID NO 2
<211> LENGTH: 335
<212> TYPE: PRT
<213> ORGANISM: Coccomyxa subellipsoidea
<220> FEATURE:
<221> NAME/KEY: misc_feature
<223> OTHER INFORMATION: WD40 repeat protein

<400> SEQUENCE: 2

Met Asp Gly Arg Leu Asn Asp Arg Arg Ala Glu Ile Tyr Thr Tyr Asp
1               5                   10                  15

Ser Glu Asn Ile Val Tyr Gly Leu Ser Trp Ser Asn Arg Arg Asp Lys
            20                  25                  30

Lys Phe Arg Leu Ala Val Gly Ser Phe Ile Glu Glu Tyr Asp Asn Tyr
        35                  40                  45

Val Glu Ile Ile Thr Leu Asp Asp Ala Thr Cys Lys Phe Thr Ser Asp
50                  55                  60

Ala Gln Leu Ala Phe Gln His Pro Tyr Pro Pro Thr Lys Ile Met Phe
65                  70                  75                  80

Met Pro Asp Lys Glu Gly Ala Gln Pro Asp Leu Leu Ala Thr Thr Gly
            85                  90                  95

Asp Tyr Leu Arg Ile Trp Gln Leu Lys Glu Asp Gly Thr Gln Leu Val
        100                 105                 110

Lys Leu Leu Asn Asn Asn Lys Asn Ser Glu Phe Cys Ala Pro Leu Thr
    115                 120                 125

Ser Phe Asp Trp Asn Glu Thr Asp Leu Asn Arg Leu Gly Thr Ser Ser
130                 135                 140

Ile Asp Thr Thr Cys Thr Ile Trp Asp Ile Glu Lys Gly Val Val Asp
145                 150                 155                 160

Thr Gln Leu Ile Ala His Asp Lys Glu Val Tyr Asp Ile Ala Trp Gly
            165                 170                 175

Gly Val Gly Val Phe Ala Ser Val Ser Ala Asp Gly Ser Val Arg Val
        180                 185                 190

Phe Asp Leu Arg Asp Lys Glu His Ser Thr Ile Ile Tyr Asp Ser Pro
    195                 200                 205

Gln Pro Asp Thr Pro Leu Leu Arg Leu Gly Trp Asn Lys Gln Asp Pro
210                 215                 220

Arg Tyr Met Ala Thr Val Leu Met Asp Ser Thr Lys Val Val Ile Leu
225                 230                 235                 240

Asp Ile Arg Tyr Pro Thr Leu Pro Val Ala Glu Leu Gln Arg His Gln
            245                 250                 255

Ala Pro Val Asn Ala Val Ala Trp Ala Pro His Ser Cys His Ile
        260                 265                 270

Cys Ser Ala Gly Asp Asp Ala Gln Ala Leu Ile Trp Asp Leu Ser Ser
    275                 280                 285

Met Ser Arg Pro Met Asp Gln Thr Leu Asp Pro Ile Leu Ala Tyr Ser
```

```
            290                 295                 300
Ala Gly Ala Glu Val Asn Gln Leu Gln Trp Ser Thr Thr Gln Pro Asp
305                 310                 315                 320

Trp Val Ala Ile Cys Phe Ala Asn Lys Thr Gln Ile Leu Arg Val
                325                 330                 335

<210> SEQ ID NO 3
<211> LENGTH: 359
<212> TYPE: PRT
<213> ORGANISM: Chlamydomonas reinhardtii
<220> FEATURE:
<221> NAME/KEY: misc_feature
<223> OTHER INFORMATION: WD40 repeat protein

<400> SEQUENCE: 3

Met Ser Ala Ser Asp Lys Arg Glu Arg Gln Glu Val Tyr Thr Tyr Val
1               5                   10                  15

Ala Pro Asp Pro Val Tyr Ala Met Asn Trp Ser Val Arg Arg Asp Lys
                20                  25                  30

Arg Phe Arg Leu Gly Val Ala Ser Phe Arg Glu Asp Val Thr Asn Tyr
            35                  40                  45

Val Asp Ile Val Ser Leu Asp Asp Glu Ser Asp Glu Leu Arg Ala Asp
50                  55                  60

Pro Gly Leu Arg Phe Pro His Asp Tyr Pro Ala Thr Lys Leu Met Trp
65                  70                  75                  80

Met Pro Asp Arg Glu Gly Cys Arg Pro Asp Leu Leu Ala Thr Thr Gly
                85                  90                  95

Glu Ala Leu Arg Ile Trp Arg Val Cys Asp Gly Ser Glu Gly Glu Glu
            100                 105                 110

Ser Gly Ser Gly Pro Gly Gly Arg Gly Val Gln Leu Arg Ser Leu Leu
        115                 120                 125

Asn Asn Asn Lys Gln Ser Glu Phe Ser Ala Pro Leu Thr Ser Phe Asp
130                 135                 140

Trp Asn Glu Ala Asp Pro Lys Arg Leu Gly Thr Ser Ser Ile Asp Thr
145                 150                 155                 160

Thr Cys Thr Ile Trp Asp Ile Glu Lys Gly Val Asp Thr Gln Leu
                165                 170                 175

Ile Ala His Asp Arg Glu Val Tyr Asp Ile Ala Trp Gly Gly Leu Gly
            180                 185                 190

Val Phe Ala Thr Val Ser Ala Asp Gly Ser Val Arg Val Phe Asp Leu
        195                 200                 205

Arg Asp Lys Glu His Ser Thr Ile Ile Tyr Glu Ser Pro Gln Pro Asp
210                 215                 220

Thr Pro Leu Leu Arg Leu Gly Trp Asn Arg Gln Asp Pro Arg Tyr Met
225                 230                 235                 240

Ala Thr Ile Leu Gln Asp Ser Pro Lys Val Val Ile Leu Asp Ile Arg
                245                 250                 255

Tyr Pro Thr Leu Pro Val Ala Glu Leu Cys Arg His Gln Ala Pro Val
            260                 265                 270

Asn Ala Leu Ala Trp Ala Pro His Ser Ala Gln His Ile Cys Thr Ala
        275                 280                 285

Gly Asp Asp Ser Gln Ala Leu Ile Trp Asp Val Ser Ala Val Gly Gly
        290                 295                 300

Gly Asn Asn Ala Asn Ala Ala Ala Gly Gly Ala Ser Asp Val Ser
305                 310                 315                 320
```

```
Leu Asp Pro Ile Leu Ala Tyr Gly Ala Ala Ser Glu Val Asn Gln Leu
                325                 330                 335

Gln Trp Ser Ser Ala Gln Pro Asp Trp Val Ala Ile Cys Phe Gly Asn
        340                 345                 350

Lys Thr Gln Ile Leu Arg Val
        355

<210> SEQ ID NO 4
<211> LENGTH: 351
<212> TYPE: PRT
<213> ORGANISM: Volvox carteri
<220> FEATURE:
<221> NAME/KEY: misc_feature
<223> OTHER INFORMATION: WD40 repeat protein

<400> SEQUENCE: 4

Met Ser Asn Ser Asp Lys Arg Ala Glu Ile Tyr Thr Tyr Val Ala Gln
1               5                   10                  15

Asp Pro Val Tyr Ala Met Asn Trp Ser Val Arg Arg Asp Arg Arg Phe
            20                  25                  30

Arg Leu Ala Val Gly Ser Phe Arg Glu Asp Val Thr Asn Tyr Val Glu
        35                  40                  45

Ile Ile Ser Leu Asp Asp Ala Ala Glu Leu Arg Ser Asp Pro Ser
50                  55                  60

Leu Arg Phe His His Asp Tyr Pro Ala Thr Lys Leu Met Trp Leu Pro
65                  70                  75                  80

Asp Arg Glu Gly Cys Arg Pro Asp Leu Leu Ala Thr Thr Gly Glu Ala
                85                  90                  95

Leu Arg Ile Trp Arg Val Leu Asp Pro Asp Ser Val Ala Gly Asp Gly
            100                 105                 110

Glu Asp Leu Arg Ala Leu Leu Asn Asn Asn Lys Gln Ser Glu Phe Ser
        115                 120                 125

Ala Pro Leu Thr Ser Phe Asp Trp Asn Glu Ala Asp Pro Lys Arg Leu
    130                 135                 140

Gly Thr Ser Ser Ile Asp Thr Thr Cys Thr Ile Trp Asp Ile Glu Lys
145                 150                 155                 160

Gly Glu Val Asp Thr Gln Leu Ile Ala His Asp Arg Glu Val Tyr Asp
                165                 170                 175

Ile Ala Trp Gly Gly Leu Gly Val Phe Ala Thr Val Ser Ala Asp Gly
            180                 185                 190

Ser Val Arg Val Phe Asp Leu Arg Asp Lys Glu His Ser Thr Ile Ile
        195                 200                 205

Tyr Glu Ser Pro Gln Pro Asp Thr Pro Leu Leu Arg Leu Gly Trp Asn
    210                 215                 220

Arg Gln Asp Pro Arg Tyr Met Ala Thr Ile Leu Met Asp Ser Pro Lys
225                 230                 235                 240

Val Val Ile Leu Asp Ile Arg Tyr Pro Thr Leu Pro Val Ala Glu Leu
                245                 250                 255

His Arg His Gln Ala Pro Val Asn Ala Leu Ala Trp Ala Pro His Ser
            260                 265                 270

Ala Gln His Ile Cys Thr Ala Gly Asp Ser Gln Ala Leu Ile Trp
        275                 280                 285

Asp Val Ser Ala Val Gly Ser Gly Gly Gln Pro Gly Ala Leu Gly
    290                 295                 300

Gly Gly Thr Ala Gly Asp Val Ser Leu Asp Pro Ile Leu Ala Tyr Gly
305                 310                 315                 320
```

```
Ala Gln Ser Glu Val Asn Gln Leu Gln Trp Ser Ser Ala Gln Pro Asp
            325                 330                 335

Trp Val Ala Ile Cys Phe Ala Asn Lys Thr Gln Ile Leu Arg Val
            340                 345                 350

<210> SEQ ID NO 5
<211> LENGTH: 341
<212> TYPE: PRT
<213> ORGANISM: Auxenochlorella prototheco ides
<220> FEATURE:
<221> NAME/KEY: misc_feature
<223> OTHER INFORMATION: WD40 repeat protein

<400> SEQUENCE: 5

Met Ser Gly Pro Ser Gly Asp Lys Arg Ala Glu Ile Tyr Thr His Glu
1               5                   10                  15

Ser Ala Asp Pro Ile Tyr Ala Leu Asn Trp Ser Val Arg Thr Asp Lys
            20                  25                  30

Pro Phe Arg Leu Ala Thr Gly Ser Tyr Val Glu Asp Gln Asn Asn His
        35                  40                  45

Ile Asp Ile Ile Val Leu Asp Glu Ala Arg Glu Gln Phe Gln Ala Asp
50                  55                  60

Pro Arg Leu Ser Phe Val His Pro Phe Pro Ala Thr Lys Leu Met Phe
65                  70                  75                  80

Leu Pro Val Lys Asp Pro Asn Gln Pro Asp Leu Leu Ala Thr Thr Ser
                85                  90                  95

Asp Phe Leu Arg Ile Trp Ser Ile Ser Glu Asp Gly Val Ala Leu Glu
            100                 105                 110

Lys Leu Leu Asn Asn Thr Lys Thr Ser Glu Tyr Cys Glu Pro Ile Thr
        115                 120                 125

Ser Phe Asp Trp Asn His Leu Glu Pro Arg Arg Leu Gly Thr Ala Ser
130                 135                 140

Leu Asp Ala Thr Cys Thr Val Trp Asp Ile Glu Arg Gly Cys Val Asp
145                 150                 155                 160

Thr Gln Leu Ile Ala His Asp Gly Glu Val Tyr Asp Leu Ala Trp Gly
                165                 170                 175

Gly Ala Thr Met Phe Ala Ser Val Ser Ala Asp Ala Ser Val Arg Val
            180                 185                 190

Phe Asp Leu Arg Asp Arg Asp His Ser Thr Ile Thr Tyr Glu Ser Arg
        195                 200                 205

Gly Gly Glu Ala Leu Val Arg Leu Gly Trp Asn Arg Ala Asp Pro Arg
210                 215                 220

Phe Met Ala Val Leu Ala Ala Gly Ser Ala Glu Val Val Val Leu Asp
225                 230                 235                 240

Val Arg Arg Pro Ala Ala Pro Leu Ala Arg Leu Ala Arg His Thr Ala
                245                 250                 255

Pro Ala Asn Val Leu Ala Trp Ala Pro His Ser Ala Cys His Leu Cys
            260                 265                 270

Ser Ala Gly Asp Asp Gly Ala Ala Leu Ile Trp Asp Val Gly Ala Leu
        275                 280                 285

Gly Gly Gly Gly Gly Pro Gly Gly Ala Ala Gln Asp Pro Gly Leu Asp
290                 295                 300

Pro Ile Leu Ala Tyr Asn Ala Gly Ala Glu Val Ala Ala Leu Gln Trp
305                 310                 315                 320

Ser Ala Ala Gln Pro Asp Trp Val Ala Ile Ala Phe Gly Asn Asn Ala
```

-continued

```
                        325                 330                 335

Gln Val Leu Arg Val
            340

<210> SEQ ID NO 6
<211> LENGTH: 351
<212> TYPE: PRT
<213> ORGANISM: Chlorella sorokiniana
<220> FEATURE:
<221> NAME/KEY: misc_feature
<223> OTHER INFORMATION: WD40 repeat protein

<400> SEQUENCE: 6

Met Gln Gln Gln Gly Glu Gly Arg Ala Glu Ile Tyr Thr Tyr Glu Ser
1               5                   10                  15

Pro His Leu Val Tyr Gly Ala Gly Trp Ser Val Arg Pro Asp Lys Pro
            20                  25                  30

Phe Arg Leu Ala Leu Gly Ser Phe Ile Glu Asp Tyr Ala Asn Arg Val
        35                  40                  45

Glu Ile Val Gln Leu Asp Glu Gly Arg Gly Val Ile Arg Ser Asn Pro
    50                  55                  60

Ala Leu Gly Phe Gln His Pro Tyr Pro Pro Thr Lys Val Gly Phe Ile
65                  70                  75                  80

Pro Asp Lys Asp Gly Thr Arg Pro Asp Leu Leu Ala Thr Ser Gly Asp
                85                  90                  95

Phe Leu Arg Leu Trp Arg Ile His Asp Glu Pro Gly Ser Asn Gln His
            100                 105                 110

Val Arg Leu Glu Lys Leu Leu Asn Asn Asn Lys Gly Gly Glu Phe Ser
        115                 120                 125

Ala Pro Leu Thr Ser Phe Asp Trp Asn Glu Leu Asp Pro Arg Arg Ile
    130                 135                 140

Gly Thr Ala Ser Ile Asp Thr Thr Cys Thr Val Trp Asp Val Glu Arg
145                 150                 155                 160

Gly Val Val Asp Thr Gln Leu Ile Ala His Asp Lys Glu Val Tyr Asp
                165                 170                 175

Ile Ala Trp Gly Gly Val Gly Ile Phe Ala Ser Val Ser Ala Asp Gly
            180                 185                 190

Ser Val Arg Val Phe Asp Leu Arg Asp Lys Glu His Ser Thr Ile Ile
        195                 200                 205

Tyr Glu Ser Pro Gln Pro Ser Thr Pro Leu Leu Arg Leu Ser Trp Asn
    210                 215                 220

Lys Gln Asp Pro Arg Tyr Ile Ala Ala Phe Ala Met Asp Ser Ser Lys
225                 230                 235                 240

Val Leu Val Leu Asp Ile Arg Tyr Pro Thr Leu Pro Val Ala Gln Leu
                245                 250                 255

Gln Arg His Gln Ala Ser Val Asn Ala Val Cys Trp Ala Pro His Ser
            260                 265                 270

Ala Val His Leu Cys Ser Ala Gly Asp Cys Gln Ala Leu Ile Trp
        275                 280                 285

Asp Leu Ala Leu Ser Gly Ala Met Gly Gly Gln Gln Gln Asp Gly Thr
    290                 295                 300

Ala Ala Ala Ala Ala Gly Gly Leu Asp Pro Ile Leu Ala Tyr Asn
305                 310                 315                 320

Ala Gly Thr Glu Ile Asn Gln Leu Gln Trp Ser Ala Ser Gln Pro Asp
                325                 330                 335
```

```
Trp Val Ala Ile Cys Phe Gly Asn Lys Ala Gln Ile Leu Arg Val
            340                 345                 350
```

<210> SEQ ID NO 7
<211> LENGTH: 355
<212> TYPE: PRT
<213> ORGANISM: Chlorella variabilis
<220> FEATURE:
<221> NAME/KEY: misc_feature
<223> OTHER INFORMATION: WD40 repeat protein

<400> SEQUENCE: 7

```
Met Gln Asp Gln Gln Gln Gly Glu Gly Arg Ala Glu Ile Tyr Thr
1               5                   10                  15

Tyr Ser Ser Ala Ser Val Tyr Ala Cys Gly Phe Ser Ser Arg Pro
            20                  25                  30

Asp Lys Pro Phe Arg Leu Ala Val Gly Ser Phe Ile Asp Asp Tyr Ala
        35                  40                  45

Asn Lys Val Glu Ile Ile Gln Leu Asp Glu Ala Ala Gly Val Val Arg
    50                  55                  60

Asn Asn Pro Ala Leu Thr Phe Gln His Pro Tyr Pro Pro Thr Lys Val
65              70                  75                  80

Ala Phe Ile Pro Asp Lys Ser Gly Thr Arg Pro Asp Leu Leu Ala Thr
            85                  90                  95

Ser Gly Asp Phe Leu Arg Leu Trp Arg Val Ser Asp Glu Pro Gly Ala
            100                 105                 110

Gln Gln Gly Val Arg Leu Glu Lys Leu Leu Asn Asn Asn Lys Gly Gly
        115                 120                 125

Asp Phe Ala Ala Pro Leu Thr Ser Phe Asp Trp Asn Glu Leu Asp Pro
    130                 135                 140

Arg Arg Val Gly Thr Ala Ser Ile Asp Thr Thr Cys Thr Val Trp Asp
145                 150                 155                 160

Val Glu Arg Gly Val Val Asp Thr Gln Leu Ile Ala His Asp Lys Glu
            165                 170                 175

Val Tyr Asp Ile Ala Trp Gly Gly Val Gly Ile Phe Ala Ser Val Ser
            180                 185                 190

Ala Asp Gly Ser Val Arg Val Phe Asp Leu Arg Asp Lys Glu His Ser
        195                 200                 205

Thr Ile Ile Tyr Glu Ser Pro Gln Pro Asp Thr Pro Leu Leu Arg Leu
    210                 215                 220

Ser Trp Asn Lys Gln Asp Pro Arg Tyr Ile Ala Val Leu Ala Met Asp
225                 230                 235                 240

Ser Pro Arg Val Thr Val Leu Asp Ile Arg Tyr Pro Thr Leu Pro Val
            245                 250                 255

Ala Glu Leu Gln Arg His Gln Ala Gly Val Asn Ala Ile Cys Trp Ala
            260                 265                 270

Pro His Ser Ala Thr His Leu Cys Ser Ala Gly Asp Asp Ser Gln Ala
        275                 280                 285

Leu Ile Trp Asp Leu Gly Leu Leu Gly Thr Leu Gly Gln Gln Pro Glu
    290                 295                 300

Gly Gly Pro Pro Gly Ala Ala Ala Gly Gly Gly Leu Asp Pro Ile
305                 310                 315                 320

Leu Ala Tyr Asn Ala Gly Ala Glu Val Asn Gln Leu Gln Trp Ser Pro
            325                 330                 335

Ala Gln Pro Asp Trp Val Ala Ile Cys Phe Gly Asn Lys Thr Gln Leu
            340                 345                 350
```

Leu Arg Val
         355

<210> SEQ ID NO 8
<211> LENGTH: 334
<212> TYPE: PRT
<213> ORGANISM: Parachlorella sp.
<220> FEATURE:
<221> NAME/KEY: misc_feature
<223> OTHER INFORMATION: WD40 repeat protein

<400> SEQUENCE: 8

Met Gln Arg Ala Glu Ile His Thr Tyr Glu Ser Pro Thr Leu Val Tyr
1               5                   10                  15

Ala Leu Asn Trp Ser Val Arg Pro Asp Lys Pro Phe Arg Leu Ala Ile
            20                  25                  30

Gly Ser Tyr Ile Glu Asp Tyr Asn Asn Arg Val Glu Ile Val Thr Leu
        35                  40                  45

Gly Glu Asp Gly Asn Gly Met Arg Pro Ser Pro Arg His Thr Phe Gln
    50                  55                  60

His Pro Tyr Pro Pro Thr Lys Leu Gln Phe Val Pro Asp Pro Asp Gly
65                  70                  75                  80

Ser Arg Pro Asp Leu Leu Ala Ser Ser Gly Asp Phe Leu Arg Leu Trp
                85                  90                  95

Arg Ile Thr Glu Asp Gly Val Ser Leu Glu Lys Leu Leu Asn Asn Asn
            100                 105                 110

Lys Ala Ser Glu Phe Cys Ala Pro Leu Thr Ser Phe Asp Trp Asn Glu
        115                 120                 125

Asn Asp Pro Lys Arg Val Gly Thr Ala Ser Ile Asp Thr Thr Cys Thr
    130                 135                 140

Val Trp Asp Ile Glu Lys Gly Val Val Asp Thr Gln Leu Ile Ala His
145                 150                 155                 160

Asp Lys Glu Val Tyr Asp Ile Ala Trp Gly Gly Val Gly Val Phe Ala
                165                 170                 175

Ser Val Ser Ala Asp Gly Ser Val Arg Val Phe Asp Leu Arg Asp Lys
            180                 185                 190

Glu His Ser Thr Ile Ile Tyr Glu Ser Pro Gln Pro Asp Thr Pro Leu
        195                 200                 205

Leu Arg Leu Ala Trp Asn Lys Gln Asp Pro Arg Tyr Met Ala Thr Thr
    210                 215                 220

Ala Leu Asn Ser Ser Ala Ile Val Val Leu Asp Ile Arg Phe Pro Thr
225                 230                 235                 240

Val Pro Val Val Glu Leu Ser Lys His Gln Ala Ala Cys Asn Ala Val
                245                 250                 255

Ala Trp Ala Pro Gln Ser Ala Asn His Ile Cys Ser Ala Gly Asp Asp
            260                 265                 270

Cys Gln Ala Leu Ile Trp Asp Leu Ser Thr Leu Gly Glu Gly Gly Ala
        275                 280                 285

Gly Gln Ala Gly Ser Pro Pro Leu Asp Pro Ile Leu Ser Tyr Met Ala
    290                 295                 300

Gly Ala Glu Val Asn Gln Leu Gln Trp Ser Ala Ser His Pro Asp Trp
305                 310                 315                 320

Val Ala Ile Cys Phe Gly Asn Lys Thr Gln Ile Leu Arg Val
                325                 330

-continued

```
<210> SEQ ID NO 9
<211> LENGTH: 337
<212> TYPE: PRT
<213> ORGANISM: Picochlorum celeri
<220> FEATURE:
<221> NAME/KEY: misc_feature
<223> OTHER INFORMATION: WD40 repeat protein

<400> SEQUENCE: 9

Met Glu His Pro Pro Ala Pro Asn Ile Leu Thr Tyr Asp Ser Ser Ser
1               5                   10                  15

Ile Val Phe Ala Leu Asp Trp Ser Arg Gln Asp Lys Gly Val Arg
            20                  25                  30

Val Ala Val Gly Ser Phe Val Glu Gly Val Ser Asn Thr Val Glu Ile
            35                  40                  45

Leu Arg Val Thr Pro Ala Gly Leu Ile Val Asp Asp Lys Glu Thr Phe
    50                  55                  60

Gly Ile Glu Tyr Pro Ala Thr Gln Val Gly Phe Ile Pro Asp Arg Phe
65              70                  75                  80

Cys Asn Lys Pro Asp Leu Leu Ala Thr Ser Gly Asp Ala Val Arg Leu
                85                  90                  95

Trp Lys Ile Ser Asp Ala Gly Thr Thr Leu Glu Leu Val Leu Asn Asp
            100                 105                 110

Pro Lys Asn Thr Ser Lys Asn Phe Ser Ala Val Thr Cys Phe Asp Trp
        115                 120                 125

Ser Glu Ile Asn Val Lys Val Leu Ala Ala Gly Ser Ser Ala Gly Arg
130                 135                 140

Leu Leu Leu Trp Asp Thr Glu Ser Gly Arg Leu Gln Gly Thr Met Val
145                 150                 155                 160

Gly His Glu Asp Glu Ile Leu Asp Cys Gln Trp Ala Ala Asn Asp Val
                165                 170                 175

Ile Val Ser Ser Ser Gly Asp Gly Ser Ile Arg Met Tyr Asp Leu Arg
            180                 185                 190

Asp Lys Asp His Cys Thr Val Leu Tyr Glu Thr Pro Arg Arg Thr Pro
        195                 200                 205

Val Pro Arg Phe Cys Trp Asn Lys Leu Asp Pro Arg His Leu Ala Phe
    210                 215                 220

Ser Ile Glu Lys Ser Arg Leu Val Ser Val Leu Asp Val Arg Phe Pro
225                 230                 235                 240

Thr Glu Pro Val Ile Leu Leu Asp Gly His Met Gly Asn Cys Thr Ala
                245                 250                 255

Leu Gly Trp Ser Pro His Arg Glu Glu Tyr Leu Cys Ser Val Gly Asp
            260                 265                 270

Asp Cys His Ala Leu Ile Trp Asp Val Gly Lys Val Asn Ser Glu Glu
        275                 280                 285

Asp Ser Lys Pro Asn Arg Glu Ala Val Asp Ala Ser Pro Ile Leu Ala
    290                 295                 300

Tyr Asn Ala Gln Ala Glu Ile Asn Ala Met Trp Asn Pro Ile Asp
305                 310                 315                 320

Pro Asp Trp Ile Ala Ile Cys Ala Arg Asn Arg Thr Gln Val Leu Arg
                325                 330                 335

Ile

<210> SEQ ID NO 10
<211> LENGTH: 412
<212> TYPE: PRT
```

<213> ORGANISM: Tetraselmis sp.
<220> FEATURE:
<221> NAME/KEY: misc_feature
<223> OTHER INFORMATION: WD40 repeat protein

<400> SEQUENCE: 10

```
Met Pro Thr Ser Asp Ala Thr Gln Ala His Glu His His Thr Leu
1               5                   10                  15

Ala Ala Thr Pro Thr Gln Gln Ala Asn Asn Ala Ala Pro Leu Ala Asp
            20                  25                  30

Arg Phe Thr Leu Gly Leu Leu Ala Met Ala Ser Gly Pro Glu Asp Arg
        35                  40                  45

Gly Ala Gly Ala Ala Gly Ala Ala Pro His Gln Arg Gly Asp Ser Asn
50                  55                  60

Gly Lys Ala Val Thr Asp Lys Arg Gly Glu Ile Tyr Thr Tyr Glu Ala
65                  70                  75                  80

Pro Tyr Pro Val Tyr Gly Met Asn Trp Ser Val Leu Leu Gln Val Arg
                85                  90                  95

Glu Asp Met Lys Phe Arg Leu Ala Val Gly Ser Phe Val Glu Asp Val
            100                 105                 110

Glu Asn Ala Val Glu Leu Ile Arg Leu Asn Glu Glu Thr Gly Lys Phe
        115                 120                 125

Glu Ser Asn Pro Ala His Lys Phe Val His Pro Tyr Pro Pro Thr Lys
    130                 135                 140

Ile Met Phe Ile Pro Asp Arg Asp Cys Ser Arg Pro Asp Leu Leu Ala
145                 150                 155                 160

Thr Thr Gly Asp Tyr Leu Arg Leu Trp Arg Val Glu Glu Asp Gly Val
                165                 170                 175

Thr Leu His Lys Leu Leu Thr Asn Asn Lys Asn Ser Glu Phe Cys Ala
            180                 185                 190

Pro Leu Thr Ser Phe Asp Trp Asn Glu Ala Asp Pro Arg Gln Leu Gly
        195                 200                 205

Thr Ser Ser Ile Asp Thr Thr Cys Thr Ile Trp Asp Ile Glu Arg Gly
    210                 215                 220

Val Val Asp Thr Gln Leu Ile Ala His Asp Lys Glu Val Tyr Asp Ile
225                 230                 235                 240

Ala Trp Gly Gly Gln Gly Val Phe Ala Ser Val Ser Ala Asp Gly Ser
                245                 250                 255

Val Arg Val Phe Asp Leu Arg Asp Lys Asp His Ser Thr Ile Ile Tyr
            260                 265                 270

Glu Ser Gly Met Pro Glu Ile Pro Leu Leu Arg Leu Gly Trp Asn Lys
        275                 280                 285

Gln Asp Pro Arg Tyr Met Ala Thr Ile Leu Met Asp Ser Ser Lys Val
    290                 295                 300

Val Val Leu Asp Ile Arg Tyr Pro Thr Met Pro Val Ala Glu Leu Glu
305                 310                 315                 320

Ala His His Lys Pro Val Asn Ala Leu Ala Trp Ala Pro Gln Ser Ser
                325                 330                 335

Ser His Ile Cys Thr Ala Gly Asp Asp Ala Gln Ala Leu Ile Trp Asn
            340                 345                 350

Leu Ala Pro Met Gly Thr Gln Gly Pro Met Gly Gly Ala Ala Pro Ala
        355                 360                 365

Val Leu Gly Ala Asp Leu Asp Pro Ile Leu Ala Tyr Asn Ala Gly Glu
    370                 375                 380
```

```
Glu Ile Asn Gln Leu Gln Trp Ser Ser Thr Gln Ser Asp Trp Val Gly
385                 390                 395                 400

Ile Ser Phe Gly Asn Lys Ile Gln Ile Leu Arg Ile
            405                 410
```

<210> SEQ ID NO 11
<211> LENGTH: 332
<212> TYPE: PRT
<213> ORGANISM: Ostreococcus lucimarinus
<220> FEATURE:
<221> NAME/KEY: misc_feature
<223> OTHER INFORMATION: WD40 repeat protein

<400> SEQUENCE: 11

```
Met Asn Ala Glu Lys Arg Ala Glu Ile Tyr Thr Tyr Glu Ala Pro Trp
1               5                   10                  15

Met Ile Tyr Ala Cys Asn Trp Ser Val Arg Gln Asp Lys Arg Phe Arg
                20                  25                  30

Leu Ala Leu Gly Ser Phe Val Glu Glu Tyr Ser Asn Lys Val Glu Ile
            35                  40                  45

Ile Thr Leu Asp Glu Glu Thr Gly Glu Phe Pro Lys Glu Ala Gln Cys
50                  55                  60

Ser Phe Thr His Pro Tyr Pro Cys Thr Lys Ile Leu Phe Ile Pro Asp
65                  70                  75                  80

Lys Glu Cys Thr Lys Glu Asp Leu Leu Ala Thr Thr Gly Asp Tyr Leu
                85                  90                  95

Arg Ile Trp Gln Val Gln Asp Asp Asn Thr Val Gln Met Lys Ser Leu
            100                 105                 110

Leu Asn Asn Asn Lys Ser Ser Glu Phe Cys Ala Pro Leu Thr Ser Phe
        115                 120                 125

Asp Trp Asn Glu Thr Lys Leu Gln Arg Val Gly Thr Ser Ser Ile Asp
    130                 135                 140

Thr Thr Cys Thr Ile Trp Asp Ile Glu Arg Glu Cys Val Asp Thr Gln
145                 150                 155                 160

Leu Ile Ala His Asp Lys Glu Val Tyr Asp Ile Ala Trp Gly Gly Pro
                165                 170                 175

Glu Val Phe Ala Ser Val Ser Ala Asp Gly Ser Val Arg Val Phe Asp
            180                 185                 190

Leu Arg Asp Lys Asp His Ser Thr Ile Ile Tyr Glu Ser Gln Thr Pro
        195                 200                 205

Asp Thr Pro Leu Leu Arg Leu Gly Trp Asn Lys Gln Asp Pro Arg Tyr
    210                 215                 220

Met Ala Thr Ile Cys Met Asp Ser Pro Val Ile Ile Leu Asp Ile Arg
225                 230                 235                 240

Phe Pro Thr Leu Pro Val Ala Glu Leu Gln Ser His Arg Ala Ser Val
                245                 250                 255

Asn Thr Leu Ala Trp Ala Pro His Ser Ser His Met Cys Thr Ala
            260                 265                 270

Gly Asp Asp Ser Gln Ala Leu Ile Trp Asp Leu Ser Ser Met Asn Gln
        275                 280                 285

Pro Pro Glu Gly Gly Leu Asp Pro Ile Leu Ala Tyr Ser Ala Gly Ala
    290                 295                 300

Glu Ile Asn Gln Leu Gln Trp Ser Ala Ser Gln Pro Asp Trp Ile Ser
305                 310                 315                 320

Ile Ala Phe Arg Asn Ser Leu Gln Ile Leu Arg Val
                325                 330
```

<210> SEQ ID NO 12
<211> LENGTH: 336
<212> TYPE: PRT
<213> ORGANISM: Micromonas commoda
<220> FEATURE:
<221> NAME/KEY: misc_feature
<223> OTHER INFORMATION: WD40 repeat protein

<400> SEQUENCE: 12

Met Ala Ala Met Gly Ser Gly Gln Ser Gly Ala Glu Ile Tyr Thr Tyr
1               5                   10                  15

Glu Ala Pro Trp Leu Val Tyr Ala Met Asn Trp Ser Val Arg Gln Asp
            20                  25                  30

Lys Arg Phe Arg Leu Ala Leu Gly Ser Phe Val Glu Glu Tyr Ser Asn
        35                  40                  45

Lys Val Glu Ile Ile Thr Leu Asp Glu Gln Arg Arg Glu Phe Pro Ala
    50                  55                  60

Glu Pro Thr His Arg Phe Asp His Pro Tyr Pro Cys Thr Lys Ile Met
65                  70                  75                  80

Phe Val Pro Asp Ala Glu Gly Thr Ser Glu Asp Leu Leu Ala Thr Ser
                85                  90                  95

Gly Asp Tyr Leu Arg Val Trp Arg Ile Gly Asp Asp Gly Val His Leu
            100                 105                 110

Arg Ser Leu Leu Asn Asn Asn Lys Asn Ser Asp Phe Cys Ala Pro Leu
        115                 120                 125

Thr Ser Phe Asp Trp Ser Thr Thr Asn Leu Ala Arg Val Gly Thr Ser
    130                 135                 140

Ser Leu Asp Thr Thr Cys Thr Ile Trp Asp Leu Glu Lys Glu Thr Val
145                 150                 155                 160

Asp Ser Gln Leu Ile Ala His Asp Lys Glu Val Tyr Asp Ile Ala Trp
                165                 170                 175

Gly Gly Pro Glu Val Phe Ala Ser Val Ser Ala Asp Gly Ser Val Arg
            180                 185                 190

Val Phe Asp Leu Arg Asp Lys Asp His Ser Thr Ile Val Tyr Glu Ser
        195                 200                 205

Pro Thr Pro Asp Thr Pro Leu Leu Arg Leu Gly Trp Asn Lys Gln Asn
    210                 215                 220

Pro Arg Tyr Met Ala Thr Met Glu Met Asp Ser Ala Lys Val Val Val
225                 230                 235                 240

Leu Asp Ile Arg Val Pro Ala Leu Pro Val Ala Glu Leu Lys Lys His
                245                 250                 255

Arg Ala Ala Val Asn Thr Leu Ala Trp Ala Pro His Ser Ser Arg Asn
            260                 265                 270

Ile Cys Thr Ala Gly Asp Asp Ala Gln Ala Leu Ile Trp Asp Leu Ser
        275                 280                 285

Ser Val Ala Gln Pro Gly Glu Asp Gly Met Asp Pro Met Leu Ala Tyr
    290                 295                 300

Asn Ala Gly Ala Glu Ile Ser Gln Leu Gln Trp Ser Ala Thr Gln Thr
305                 310                 315                 320

Asp Trp Ile Ala Ile Ala Phe Gly Lys Asn Leu Gln Val Leu His Val
                325                 330                 335

<210> SEQ ID NO 13
<211> LENGTH: 346
<212> TYPE: PRT

<213> ORGANISM: Arabidopsis sp.
<220> FEATURE:
<221> NAME/KEY: misc_feature
<223> OTHER INFORMATION: WD40 repeat protein

<400> SEQUENCE: 13

```
Met Gly Thr Ser Ser Asp Pro Ile Gln Asp Gly Ser Asp Glu Gln Gln
 1               5                  10                  15

Lys Arg Ser Glu Ile Tyr Thr Tyr Glu Ala Pro Trp His Ile Tyr Ala
             20                  25                  30

Met Asn Trp Ser Val Arg Arg Asp Lys Lys Tyr Arg Leu Ala Ile Thr
         35                  40                  45

Ser Leu Leu Glu Gln Tyr Pro Asn Arg Val Glu Ile Val Gln Leu Asp
     50                  55                  60

Glu Ser Asn Gly Glu Ile Arg Ser Asp Pro Asn Leu Ser Phe Glu His
 65                  70                  75                  80

Pro Tyr Pro Pro Thr Lys Thr Ile Phe Ile Pro Asp Lys Glu Cys Gln
                 85                  90                  95

Arg Pro Asp Leu Leu Ala Thr Ser Ser Asp Phe Leu Arg Leu Trp Arg
            100                 105                 110

Ile Ala Asp Asp His Ser Arg Val Glu Leu Lys Ser Cys Leu Asn Ser
        115                 120                 125

Asn Lys Asn Ser Glu Phe Cys Gly Pro Leu Thr Ser Phe Asp Trp Asn
    130                 135                 140

Glu Ala Glu Pro Arg Arg Ile Gly Thr Ser Ser Thr Asp Thr Thr Cys
145                 150                 155                 160

Thr Ile Trp Asp Ile Glu Arg Glu Ala Val Asp Thr Gln Leu Ile Ala
                165                 170                 175

His Asp Lys Glu Val Phe Asp Ile Ala Trp Gly Gly Val Gly Val Phe
            180                 185                 190

Ala Ser Val Ser Ala Asp Gly Ser Val Arg Val Phe Asp Leu Arg Asp
        195                 200                 205

Lys Glu His Ser Thr Ile Ile Tyr Glu Ser Ser Glu Pro Asp Thr Pro
    210                 215                 220

Leu Val Arg Leu Gly Trp Asn Lys Gln Asp Pro Arg Tyr Met Ala Thr
225                 230                 235                 240

Ile Ile Met Asp Ser Ala Lys Val Val Leu Asp Ile Arg Phe Pro
                245                 250                 255

Ala Leu Pro Val Val Glu Leu Gln Arg His Gln Ala Ser Val Asn Ala
            260                 265                 270

Ile Ala Trp Ala Pro His Ser Ser Cys His Ile Cys Thr Ala Gly Asp
        275                 280                 285

Asp Ser Gln Ala Leu Ile Trp Asp Ile Ser Ser Met Gly Gln His Val
    290                 295                 300

Glu Gly Gly Leu Asp Pro Ile Leu Ala Tyr Thr Ala Gly Ala Glu Ile
305                 310                 315                 320

Glu Gln Leu Gln Trp Ser Ser Ser Gln Pro Asp Trp Val Ala Ile Ala
                325                 330                 335

Phe Ser Thr Lys Leu Gln Ile Leu Arg Val
            340                 345
```

<210> SEQ ID NO 14
<211> LENGTH: 12
<212> TYPE: DNA
<213> ORGANISM: Oocystis sp.
<220> FEATURE:

```
<221> NAME/KEY: misc_feature
<223> OTHER INFORMATION: partial sequence of WD40 repeat protein

<400> SEQUENCE: 14
agactcgcac cg                                                        12

<210> SEQ ID NO 15
<211> LENGTH: 1643
<212> TYPE: DNA
<213> ORGANISM: Oocystis sp.
<220> FEATURE:
<221> NAME/KEY: misc_feature
<223> OTHER INFORMATION: WD40 repeat protein, 3EUKG2027500, encodes SEQ
      ID NO: 1

<400> SEQUENCE: 15
atggccgagc cggacgcgaa cggcgcgtcg gatggcaagc gcgcggagat ttacacgtac    60
gagttcccca acctcgttta ctccatgaac tggacggtaa gcaagcacag ttgtagcgca   120
cacagccttg ggtgctgctg cgtccttgct gatggtcatg cttgcgtcgg ccacccgttt   180
tctcacctac cgaaactggc tgcgcacccc tttcagttat gcttgtaatc accgcctcat   240
tacctttgtg tgcagtctcg tcgggacaag aagtttcgac tggcagtggg cagcttcatc   300
gaggactata ataacgtcgt caatatcata tcctgtacgc gccttccccg cactacccag   360
cgtagcggct cagtctgtcg tgcggggttg gcacgacagt cgttgggttg aagactattt   420
gaactattgc tgattagtga cgcccatgct ctctcgtaaa gcgggcgga tggctccttt    480 cgcgcccact accatctggc cgcgacctgt ggctctgacg cctcgctggg tctcgacctg   540
ctgaccatac tccctcgtta ctggctgcaa cgcagtggac gaggaacagg gcaagtttgt   600
atgcgacccg tcactgacct tcaagcatcc gtacccaccg accaaggtga tgtttgtgcc   660
agaccgggaa ggcactcggc ccgacctgtt ggccaccacc ggcgactatc tgcgcgtgtg   720
gaagatcggg gaggatggcg tcacgctgca aagctgctg aacgatgtaa ggcctagatt    780
aacgtccagc gctgtgggga aggaccgacg gcacgggccg gaaagggaca tgcatgccgt   840
accgggggtg atcacgggcg acggcccacc ggatcatcat cttcctcgct tccaccaacc   900
ctgcgcaacg tccttcgcaa cgtcttgaac aatattttgc atctttcacg ttcatccatc   960
ctcgtcatgg cgaaattaac ttgcagaaca agaacagcga gttttgcgcg ccgctcacat  1020
cgttcgactg gaacgagacc gaccccaagc gcctgggcac cagctctatc gataccacgt  1080
gcacgatctg ggacatcgag aagggcgtgg tggacacgca gctcatcgcg cacgacaagg  1140
aggtgtatga catcgcgtgg ggcggcgtcg gcgtcttcgc gtcggtgtcc gccgacggct  1200
cggtgcgagt cttcgacttg cgagacaagg agcatagcac gatcatctac gagacgccgt  1260
cgccagagac gccgctgctg cgcctggggt ggaacaaaca ggaccccagg tacatggcga  1320
cgatcgtgat ggactctaac cgcgtggttg tgctggacat ccgcgtgccc accgtgcctg  1380
tcgccgagct gcagcggcac caggcgtgcg caaacgcgct tgcctgggcg ccgcacagca  1440
gctgccacat ctgcacagcg ggcgacgacg cacaggcgct gatctgggac ctcagcgcgg  1500
tatccaagga gggcgactcg ggcctggacc ccatcctcgc gtacaatgca ggtcaagagg  1560
taaaccagct gcagtggtct tcgacgcagc ccgattgggt ggcagtctgc tttggcaaca  1620
aggcgcagat cctgcgagtg tga                                         1643

<210> SEQ ID NO 16
<211> LENGTH: 1023
<212> TYPE: DNA
```

```
<213> ORGANISM: Oocystis sp.
<220> FEATURE:
<221> NAME/KEY: misc_feature
<223> OTHER INFORMATION: WD40 repeat protein, cds of 3EUKG2027500,
      encodes SEQ ID NO: 1

<400> SEQUENCE: 16
atggccgagc cggacgcgaa cggcgcgtcg gatggcaagc gcgcggagat ttacacgtac      60
gagttcccca acctcgttta ctccatgaac tggacgtctc gtcgggacaa gaagtttcga     120
ctggcagtgg gcagcttcat cgaggactat aataacgtcg tcaatatcat atccttggac     180
gaggaacagg gcaagtttgt atgcgacccg tcactgaccct tcaagcatcc gtacccaccg    240
accaaggtga tgtttgtgcc agaccgggaa ggcactcggc ccgacctgtt ggccaccacc     300
ggcgactatc tgcgcgtgtg gaagatcggg gaggatggcg tcacgctgca gaagctgctg     360
aacgataaca agaacagcga gttttgcgcg ccgctcacat cgttcgactg gaacgagacc     420
gaccccaagc gcctgggcac cagctctatc gataccacgt gcacgatctg gacatcgag     480 aagggcgtgg tggacacgca gctcatcgcg cacgacaagg aggtgtatga catcgcgtgg    540
ggcggcgtcg gcgtcttcgc gtcggtgtcc gccgacggct cggtgcgagt cttcgacttg    600
cgagacaagg agcatagcac gatcatctac gagacgccgt cgccagagac gccgctgctg   660
cgcctggggt ggaacaaaca ggaccccagg tacatggcga cgatcgtgat ggactctaac    720
cgcgtggttg tgctggacat ccgcgtgccc accgtgcctg tcgccgagct gcagcggcac   780
caggcgtgcg caaacgcgct tgcctgggcg ccgcacagca gctgccacat ctgcacagcg    840
ggcgacgacg cacaggcgct gatctgggac ctcagcgcgg tatccaagga gggcgactcg    900
ggcctggacc ccatcctcgc gtacaatgca ggtcaagagg taaaccagct gcagtggtct    960
tcgacgcagc ccgattgggt ggcagtctgc tttggcaaca aggcgcagat cctgcgagtg   1020
tga                                                                   1023

<210> SEQ ID NO 17
<211> LENGTH: 4908
<212> TYPE: DNA
<213> ORGANISM: Chlamydomonas reinhardtii
<220> FEATURE:
<221> NAME/KEY: misc_feature
<223> OTHER INFORMATION: WD40 repeat protein

<400> SEQUENCE: 17
atgagcgcga gcgacaagcg cgagcggcag gaggtttata catatgtggc accggacccg      60
gtgtacgcca tgaactggag cgtgagttgc cctcgggcac ggctatgacg ggcgctcgct    120
gggctgctgg ggacggggct tgggaaggcg ggaggcccgg cgccgtctgc agaccctgcc    180
gctttgtttg ggtggatagg actgtgtcgc ggcaaacgtc cttgcggact gcactggctt    240
gaatgccatg agccaagggg cgctgtggag aggcagagca gagggcgggg atgccaagca    300
gcgcgtggcg tggcggccgc cgcccctgcc tacacctgac tgccctcggg gctgccgacg    360
attgctgact cgctgtacga caaattggcg tgccagaggg ccggggctgt gggatggcga    420
tggcagtaac attctgcaag catgcctctg ctgtgccacc acgtgctcac acacccacac    480
tcgcctgcac ccgctaactt gcccatgacc cacacctaca ccccgcacaa ccctgcacac    540
ccgcacccgc aaccataccct accacaggta cggcgggaca agcgcttccg actgggcgtt    600
gcttcattcc gggaggacgt caccaactat gttgacattg tgtcgcgtga gtccaggcgc   660
acacggggcg attgagtaac atggggattg cggacggcag ttacactgtt acggggtat    720
```

```
gaagtggagc tgtagagtac agccggagat aagcacatcg ttcggcacag agggagtgtg    780
tcttggcctt gcccacccca cactgctcca cttccccgcc tccccgcctc ccgctcccc    840 gcctcccccc cgcccccgc ctgccccagt ggacgacgag tcggacgagc tgcgggcgga    900
ccccgggctg cgcttcccgc acgactaccc ggccaccaag ctcatgtgga tgccggaccg    960
cgagggctgt cggcccgacc tgttggcgac cacaggtgcg gcggggctgt ggcggtggtg   1020
gtggtggtgg tggcggcggt cgtggtggtg gtgtggcgg cggtcaggga tgggatgtgg   1080
gttgggggat tgttcgagat gtctggcgca ggtacaagtg gccgggctgg cagcagtgct   1140
gcacttggta acactgccgt tatgtgtctg acacaagccg cacacacgtc tgggctggta   1200
catgcacctg cttcggccgg tttacacgga ttacccgcca acacacacac acacacacac   1260
acacacacac gcacacacac acgtgcacac acaaccacca cacaggggag gcgctacgca   1320
tctggcgtgt gtgtgacggc tcggagggcg aggagagcgg cagcgggccg ggcggacgcg   1380
gcgttcagct gcggtcactg cttaacaacg tgagcggcgt gcggggcgcg cgtttgcgct   1440
gtgtacgctg tcatgttagt gttaggggc acatgggaag gcaaacgggc agggcagtgt   1500
gtgcgctgcg tgatctgtgt tgcggtggtg tgtgcgggcc gtgtgccgtc atggggctg    1560 cgtgtcgcgt gcctgcatag gttgtggggt tgtgtgtatg tgtgtgtggg cgatcacaat   1620
gtggggttcg gacccgggtg tgaggagggt tgggcgggtt gcgcgaactc atcagagcgg   1680
cagctgcgct cacgctgcaa gcccatccaa atctacggtc acaactgttt gcacacccac   1740
gaacccttca aacaaaccgc ccaaacccgc atcaacgttc tcgcacctcg cagaacaagc   1800
agtcggagtt ctcggcgcca ctcacgtcct tcgactggaa cgaggccgac cccaagcgcc   1860
tgggcacctc ctccatcgac accacctgca ccatctggga catcgaggtg cggcgcggat   1920
ggcggcgtgc ggcgtgtggc gtgtggcgtg ggatggaggc tggtggtggt ggcggcgttt   1980
cgtccgccct tgcttaacgt ctcacctccc tggagtgacc tgcagtcgct caccgcggct   2040
gtgtgcgtcc tctgtgcctt acgcctccac cgcccccccc catcgcccag caagccatgc   2100
cagtaccccc cccttagct agtcatgaag gtaaacctcc cccgccccac ccctcgtctt   2160
cggagccctg ccaagctcct cccccacctc ctcccccgcc ggcacctgct gtctacttcg   2220
ctacacttct ctgtaccaat ccttgcaacc cccgccggca acgacgcggt tgctgtgcca   2280
ctgtgcctgg ctacaacttc acttcttggt ttattatgaa tgtagtaacc catctcccca   2340 ccacccctc ctctccccca cctgcagaaa ggcgaggtgg acacgcagct catcgcgcac   2400
gaccgggagg tgtacgacat agcctggggt gggctgggcg tgttcgccac cgtcagcgcg   2460
gacggcagcg tgcgcgtgtt cgacctgcgg tgagcggagg ggggcgaga gggcgggagg   2520 gagggaggga gggcatcggg atgggggcc gggcgggagg gaggccttt catgttatga    2580 tcacagtttt ggagcgctgg cggggatgg cgaggtggtt cacctaaaag caaccatgac   2640
acacgaagat gtagggcagg cgtgggtgcg cgcggggagg gggctgaaag gcgtgcgcct   2700
gcgtggtacg gggttcgtgt ctacggcgca tgggggtcg tggctgctgc caggcctgtc   2760
gggcgggtgg cacgtggcac gtggcgggtg gactgctggt caaactccga cattcccagt   2820
cccagcccat gtccgcacgg gtcccgagcc actcccatcc cgcccttcct cccgcccgc    2880 atccccatc tcctcctccc cctcgccgca gcgacaagga gcactcgacc atcatctacg   2940
agagcccgca gcccgacacg ccgctgctgc gcctgggctg gaaccggcag gaccccgct    3000 acatggccac catactgcag gtgtgcgcg gctgggtata tgtatgtgtg tgtgtgtta    3060 tatgtgtgtg tgtgtgtagc agctggtggc atttgcgctt ggcagccatt ggccgttggc   3120
```

```
aagacaggca ggaacaattc acgatttgga gagcgggacc gttgatgtga tcaggtggcg    3180
gtttgaagcg aacatcaggg tgtgtgggtg gggggggggga tcagcaacag gctaacgcg    3240 gcgggcgcct cagtgcggca ctgacagctg cacgcggtgg cggcaggcga gcgcaaacgt    3300
ggagcgcaag cgtttgctgc gtcgccagtc gcgcgagtgc attgctgtca ctggcggcat    3360
ggtggtggtg atggcggtat tgtcatgct ggctcagccc ctttccctct ctccctctcc    3420
accacatccg cccttgcgc tctgtctttc gtggcccatc catctcctcg cctgcctgc    3480 aggactcgcc caaggtggtc atcctggaca tccgctaccc caccctgccc gtggcggagc    3540
tgtgcaggca ccaggtgcga ggcggcgag cggttgtgtg cagggcggcg gcggtgggtg    3600
ggtgggttgg ttggtttcta gctgccaggg ttacggcagg ggaaggagca aagacagagc    3660
gatggcagtg cgggcgattg tcgattggag ccagtcgcgg ggtctcggag ggcccagc     3720 acttgcagtt gaaaggcgct gggttttgcg aggtgaaacg gattgtgttg tgttattgga    3780
gttgcgggac ctttcatttg ctgtgctctg tgccgctgtt tcctcacagg cgccggtcaa    3840
cgccttggcc tggcaccgc actcggccca acacatctgc accgccgggg acgactcaca    3900
ggtgtgcaca aggggtggcg gaatgggca ggcagcgtgt gtggttgtgt gcggtggttg    3960
ggggttgcaa ggattggtac agagaagtgt agcgaagtag acaacaggcg tggggtggat    4020
ttccagcgtg gcttgtactc gagctcctct ccgttggtgt gaccgccaag ccaagccggg    4080
ctgcttccga agctgttttc gtcagcccca tcaccggtgc ccggccacct ctgcaaagcc    4140
cgcgcctcgc gctcgcccca acgcaaccct tgcctcgcac cccgtctgcc cacccacgca    4200
caggcgctga tctgggatgt gtcggcggtg ggcggcggca acaatgccaa cgcggcggcg    4260
ggcggcggcg ccagtgacgt cagcttggac cccatactgg cgtacggagc ggccagcgag    4320 gtaaggggg tttctgggga ctgggtcttt ggggctgggg ttctggtgtt tgcgtgtgtg    4380 ggggggggt gtatgtgtgt gaaagaagaa acgaaacga tgtgtgtgtg tgtgtgtgtg    4440
tgtcagagag caaggaaaca caggagagag tgtgtgtgca tgtgtgtgtg ttagaaataa    4500
cacgagatag gtgtgtgtat gtgtgtttgc aagcatgcac caaacccagc cgcgaaccca    4560
tcctgtcggt gaggtgcgaa gggtggaggg cgtgggttac agcggtgtag tttgcttcag    4620
ctggttgagt gcattggaaa ggcgtgcgcg tcagaagggc tcgcgcgacg agaagagggg    4680
tgtgttccgt gggcattggg ggtgctgtgg gtggtggcga agaggagggg cggcgccgaa    4740
gggcctgcgg tttgggctgg gttcgttgcc ggtgctgctc cggccttgtt gcgccccaac    4800
cggcatcccc catcacaatt gcaggtgaac cagctgcagt ggagctccgc gcagccggac    4860
tgggtggcaa tctgcttcgg caacaaaacg cagatcctaa gggtgtga                4908
```

<210> SEQ ID NO 18
<211> LENGTH: 5770
<212> TYPE: DNA
<213> ORGANISM: Coccomyxa subellipsoidea
<220> FEATURE:
<221> NAME/KEY: misc_feature
<223> OTHER INFORMATION: WD40 repeat protein

<400> SEQUENCE: 18

```
gcttgagcgc acaccagata agtgccaagt tcaccatcgc acgtagcaat ttggcagctg     60
ccaactgttg aacacccatt ggtgatcaag gttaggaaaa accacgaact ctgcaggagg    120
atcaaggatc aaatcttgaa gtgatgatag ttggatctca atggtagaat ggatgggaga    180
ctgaatgaca gacgggcgga gatatacacc tacgactctg agaacatcgt atatggcttg    240
```

-continued

| | | | | |
|---|---|---|---|---|
| agctggagtg | taaggatcca | ttcagtctat | cttcctgaat | ttaattgctg | cattatgtat | 300 |
| tgttccactt | gccctgggt | caagtcagtc | catgcactct | tacttgctac | ccctctggag | 360 |
| acacagactg | actggattgt | tctccttgct | gggctgcaga | accgccgtga | caagaagttt | 420 |
| cgcctggcag | tgggcagctt | catcgaggag | tacgacaact | acgtcgaaat | catcacacgt | 480 |
| gcgtgccgtc | ctagtctcac | cttttgcacc | ttcacctgca | ccgaacctgc | cctcccctgc | 540 |
| ttgtgaaact | ctcctcaaac | cacagttgag | ccacatgcaa | gaaacagagg | aagatccgac | 600 |
| accaccggct | gtttattgct | caacttgatg | ataattacga | gatgaatttg | catgagggta | 660 |
| ggactggggt | gagaggggta | gagcactcct | tggatggccc | aaagccatac | cacttacaga | 720 |
| ccctcttcca | ccaatgtgtt | gcagacaggc | ttagtgcgca | aggagccaga | aactgagatc | 780 |
| agatgatacc | accaaactgt | tgaagacagg | gctttgggtg | cgaaggtcca | aagcagaggg | 840 |
| gaaaagatag | attcggtgct | gcagaaaggc | ttgcataagc | taagattcag | acactctcac | 900 |
| caatctgttg | cagacagtct | atggacgcaa | gggtgcaaaa | attgagatcc | atatattctt | 960 |
| taccagtctg | ttgcagacag | gctttggctg | cagaggccca | aagccgagga | agaaagtttg | 1020 |
| gttcgggtgt | gtagacaggc | ttgcagaacc | agaggtccac | gtactctgac | cagtctgtta | 1080 |
| cagacagatt | cttggggtgc | agaggcataa | agcagacggg | gaaagattga | ctgggttgtc | 1140 |
| caaacaggct | ttgtgcaggc | aggctctatg | cagacaggcc | tttaagtgca | gcttgagaag | 1200 |
| cagagaccca | gacactctca | ccaagctgct | gcagacaggc | atgggatgca | agggtccaga | 1260 |
| gcagagctga | gagggagaaa | gcggttcggt | tttacatgac | gcctgcagac | agtccgagac | 1320 |
| aggcttgcag | aataatacga | ttatctgttc | gatagcacaa | cgtgcaaatt | catcacagat | 1380 |
| aagctctggg | tgcaaagctt | cagaagttga | attccagatg | ctctcaccca | tgacaggcgt | 1440 |
| gggtgacaaa | gctccagaag | ctgagaggga | aagagtggtt | cggttgtaca | ggacgcctgc | 1500 |
| agccagtctt | gagacaggct | ggcagaggct | gacaggaga | cattgttgt | ctgcgcaatc | 1560 |
| gatgacatga | catgcgagtt | cacatcggac | gctcagatct | agacaccctc | accaatgcgt | 1620 |
| tgcagacagg | gctctggatg | caacgctgca | gaagctgagg | agggctggca | ttgtctggcc | 1680 |
| catcagggct | ttttgccgt | cgtcaattcg | ccgttagggg | gagtttatga | ttgcagcgag | 1740 |
| gtgtagattt | tagggttcga | ttttagggtt | taaggtttaa | aaccttattc | ccccgtgacg | 1800 |
| gcgacgacga | tgaaaaagc | catatgcctg | ggctgagcag | acgggcttgg | gttgccaaac | 1860 |
| ttaaaaattc | gagaatgaac | caggggtgtg | tggtgcgcgc | agtcgatgac | gcgacatgca | 1920 |
| agttcacgtc | ggacgcgcag | ctggcgttcc | agcacccgta | cccacccaca | aagatcatgt | 1980 |
| tcatgccgga | caaggagggg | gcgcagccgg | acctgctggc | aaccactggc | gactacctgc | 2040 |
| gcatctggca | gctgaaggag | gacggcacgc | agctggtcaa | gcttctcaac | aatgtgcgcc | 2100 |
| tccttcccta | gtaaaattgt | ctgtttatta | gtatcccacg | ctgttgatat | ccccgggga | 2160 |
| gattgcgcag | cctcaaacaa | gcttcaggta | aaggtcgaca | gctgaaggag | gacggcactc | 2220 |
| agctgatcaa | gctgctgaac | aatgtgcgcc | cgctctcaga | aagacaaatg | gagaaagaag | 2280 |
| tatgcagaca | tcaggcagcg | cgagcgctag | aagatagaag | aaagggctgg | ctcacaagtg | 2340 |
| cacgtcatgc | aacaacaata | caatgatacc | cagccctgac | aattcttgtt | attgtgaaca | 2400 |
| catgctgtca | gattacccc | ctcctaccaa | gggggggaag | gtgcggctgc | aaacaagctt | 2460 |
| caggtgacag | atggctgctg | aaggaggatg | gcacgcagct | ggtcaatctg | ctcatggatt | 2520 |
| tgcgcctgct | ccagcatagt | gaccaattat | tgtaatcttc | acatgttgtg | tgcaattgtg | 2580 |

```
tattttctcc ttcgcgccga cagggcccgc cactgtaggc aggatacggc ttacagacgc    2640
ggtaggaacc tactagagat tgtggtggc tgcagcttac ggtgcctgcc atgtagatga     2700
cggaacccat ggtgtggtgg tggtaatggg tttgggccac atgctgtgat gtgctgccct   2760
tctgtatcag agcagtgcat ctcacttcct ggttcaggct gacggattgg aaataactga   2820
gctcaacatc ggaactaagt cttcaatcc agaaggccct tttcgtcgat cttcgcacgg    2880
aagtggaagt gcagccgccc caatatctgg ttcaagctgg actcttcag gcaggactgg    2940
caggactgag gcttgcttgc gtagttgagc ttgtgcagcc gccacccctg tgcgctggaa   3000
gttagcagtg ctgaattgtg tgtggcttat gtgtgaacta tctgcgcaga acaagaacag   3060
cgagttctgc gcaccgctca cctccttcga ctggaacgag accgacctga atcggctggg   3120
gacgtcgagc atcgacacca cgtgcaccat ctgggacatc gaggtgactc gctcacaccc   3180
ttgcaccatg atttcaaggg tcttgaacta cagtaagaca catattttct ggcttgcgta   3240
ggggccagag cacagtgtcc cctgagctga gaatccctg tgtgactagc tttacatgga    3300
agcctaacca gatcgcctca tgcagtccta gtcacacagg ggactctttg ttgtatgatc   3360
ttattgaaag atcttttcta gtctcaaagg ggactcttta cctaacgtca aatcagcgcg   3420
ctctgagtgg catatcagat aagggagtgt gtctcaatgt atgtcaccaa ctggacccta   3480
aggccagtct gacctctagg tggttcctca catgatagac cggtactgag catgtcactg   3540
agctgagctg gcggtcgcgt gattgtctct gcagaaaggc gtggtggaca cacagctcat   3600
agcgcatgac aaagaggtct atgacatcgc ttggggcggc gtgggagtct ttgcgtcagt   3660
ctcggctgac ggctctgtgc gcgtatttga cctccggtgc gccctgaac tggcaggtgt    3720
cgattgatga gctggcgctg gctcattggg cgatattgga agtgtcttag ggagttcatt   3780
tccttgcata gcagtcagga gagtacttgc atggacaatg gaactcgatg acaaaggcag   3840
ccctcccatg ttcgccccac accctactcc cacacctgaa gcaagaggtg aagtgggact   3900
tgtgagggca gaagcacatt gtactggtgt ttacagaaga ctacctctta cgggcctgag   3960
tgccagctgc tgggtctcac aaaagcgccg aaaaaattgc actccttcc cttgctgcca    4020
aggtctttct tggcgactgc tagagtgacg aagaagtctg taagcaggtt tgaagctcct   4080
tggcactgtg attgtgatca gcgggggggct tgtttgctga tcagcaagga gtgcattgct   4140
gcctgcagat atcatgcagg ctatgcatcc ccgcccctcct atctggtgcc ttcatatttg   4200
caggtctacc tcaaactttg gggtacagtg catcacattg aggtgccgct tttgcaggga   4260
caaggagcac agcacgataa tctacgcacg cccgcagccg gacacgccgc tgctgaggct   4320
ggggtggaac aagcaggacc cccgctacat ggccacagtc ctcatggact ccaccaaagt   4380
ggtcatcctg gacatcaggt gacacactgt gcttacgctt ctttgaataa ttgcactgta   4440
acgggcggcc ctcttctctg cagtttctga atttctgaat ccattacctc tctttaaacg   4500
ctgaatggag tgtactacgc tgggtttgcc cattatgtca acattaacaa tgaacactgt   4560
aattaggaat aataatatgg ctgccagcaa ggtggagggc ttgccaggca tcttcaggca   4620
ccgccctgtg cgcctcggaa aatagaattt caaacttgaa tttggcactt gtgccgcggc   4680
aggtaaccgt ctaggtccac accctcctgg gatgtcagac cctgcttgag cctcggggac   4740
tctatttcca cctttgtact tttcacccag agggcccaga tgagctgtaa gtggggcgac   4800
ccgtcgcatg agcttgaatt caaaagctgt gccgtggcag gtatccgacc ctgccggtgg   4860
cggagttgca gaggcaccag gcgccggtga acgcggtggc gtgggccccc cactcctcgt   4920
gccacatctg cagcgcgggg gacgatgctc aggcgctgat ctgggatctc tcttccatgt   4980
```

```
ctcgccccat ggaccagacc ctgggtgagc ccaccttgat ctagatcatg tgtatctcat      5040
ttgctacacg cctgtcctgc caaaagtcaa gattaattct tgcagacaag ctgcagtaaa      5100
aggctgccac aacctacccc tcgttggcct cgccaaatgc aagcaagacc caatcaaccg      5160
taggcacggt gctcgagctc agtgtttaca ccgcccctg tcagactggg cgtccatgtg       5220
gcaggaatgc tgcaaggagg gagctcgtcg ggttgatggt gtgtgggaag gagtgggcgg      5280
aagattgttg tgcttgaggg gcatacatgt tgtcaaggca tgatgtgctg tgctgcgcag      5340
atcccatcct ggcatacagc gctggggcgg aggtgaatca gctgcaatgg tccacgacgc      5400
agcctgactg ggtggccatc tgctttgcaa caagaccca gatcttgagg gtgtgagggg       5460
attgcgaacc tgtgaggcgt ttgtctcagt ccaattaaat ctgtgaaggg gtgccagaat      5520
ggatgtacag gagcgtcgag tagaattcta tattcttggt atcgggttac gttcgggttg      5580
ttcctgttgg aacggttgag ctgtgtttta gttctgcctg tctggcacaa aaaaatgtct      5640
gttctggtcc ccgtggactg tgaatgagag aaccggctga gatctttgag aacctattga      5700
catgaaggtt gcagcacatt aagaaaagga ggagcgctct tggtaacctt gctgtaacgt      5760
tgctagatgc                                                             5770
```

<210> SEQ ID NO 19
<211> LENGTH: 5079
<212> TYPE: DNA
<213> ORGANISM: Volvox carteri
<220> FEATURE:
<221> NAME/KEY: misc_feature
<223> OTHER INFORMATION: WD40 repeat protein

<400> SEQUENCE: 19

```
atgagcaaca gcgacaagcg tgcggagatt tatacctatg tggcccagga ccccgtctat       60
gcgatgaact ggagcgtaag tgtcggactt tggtgttttt tctccctctt cgcaactcga      120
gccactcata gtcactcgca cttaagggtc gtaacgtatc gcctgacggg atggtactgg      180
ggtcatgggg ctgacaacca ccgctagctc actttgcatt cccgggctgt gggggagggt      240
ggtgtgaggg cggggaggac ggcacaacgg gtggcagtgc gtagcccctg tccatgccat      300
agtttaaatg ctgcttggag cttgcgttga gctctcgaca cccccatgcc gccgccttag      360
atgtaaggga gcagtaggga cgtcggtgag cgggcccctc ttaaccccct ttccacaacg      420
aaatacacac gcacaccgtg tcggcccggc ccagtcactc cagcccccat ggctttctc       480 tccccgccga caggtccgcc gtgaccgcg ctttcggttg gcggttggtt cgttccgcga       540
agatgtaacc aactacgtgg aaatcatcag ccgtgagtac ggcagctacg tcggtgatgg      600
ggtcccgtct ctagggtgcc acataaggtt gccccttttg ctaagtgtcg ttgttgatac      660
tgttgttgtt gtggtggtgg taatggtaat ggtaatggta atggtaatgg taatggtgat      720
gatgatggtg ggcgtgggtg tgctttgggt gttgcgcatg ggaagtgcgg cttccctccg      780
cccactctcc aacccactct ccccttcccc tccccccca cacacacact cacacacacg       840
cagtggatga cgatgctgct gagctgcgct ccgacccctc cctgcgcttc caccacgact      900
accccgccac caagctcatg tggcttcccg acagagaggg ctgcagaccc gacctgctag      960
cgaccacggg ggaggcgctt cggatctgga gagttctgga tccggattca gttgcggggg     1020
acggggagga cgtggcggcg gcggggggcag gggaggagg agcgacgggt gttggcggg     1080 gtgtgcagct acgagctctg ctgaataacg tgagtttggt tttggggagg ggggccgccg      1140
tgcgtttggc tgcgtttggg gcggggacc cctgagatag gttcgtatca ttagctaata      1200
```

```
tacttaatat cttgaatatt cctggatttt gcttttacgc tagcagaact tgctattgca      1260
cgtacaccat tattatccat taccgaacca ggaaattacc ataccgccaa gcaactggtc      1320 acagccette tgccccaccc ccgggtgccc ccgggtccgg ctcctgctcc cccctteccc      1380 cccgcccacg gctcattgaa accggccacc cttcagcggc aactgatatc cgatattcct      1440
cagagcttat cactgcagat gaaccttcaa tttactttt attcctatcg acacgggcgc      1500
agacttgttg ccctatcccc tgtggtaggg cccgttcttt gactttggca tcatcacgta      1560
actgaggtgg ccccaggtga ccgacttgac taacattgat gtgccccttc ctgtgctggt      1620
gctggtgctg gtgttggtgt tggtgttggt gttgttcaga acaagcagtc cgagttctcc      1680
gctccgctga cctccttcga ctggaacgaa gcggacccca gcggctggga acctcctcc       1740 atcgatacca cctgcacgat ctgggacatc gaggtgtgtg gagcgtgagg gtggggggc       1800 cctctggggg gctgtggggg ttgggggag gggaaggtgg gagggaaac ccgctgatcc        1860 cggggtttgg gaccgttgga tttgcgcggg acatgggtat aggggtttcg ggggatcggg      1920
gtttgagctg gggagctgtg gcgtgttggg agagagaagg gagggaaggg tgtgctgagc     1980
ggtgggtttc gtggggctga tgtgtttttt tatgtgagat gtgtgccggt gttgtgggct     2040
tatgtttcct cccttttcga ccctctgcac ccctctggcc ttcttcctta cacatcacct     2100
agatcccgtt ccccctcctc tctcttcgcc tctccgcccc catacacaca accacattga     2160
tcgcgtaaag aaaggggagg tggacacgca gctgattgca catgaccggg aggtgtacga     2220
catcgcctgg ggaggactgg gggtatttgc aaccgtgtcg gcagacggct ccgtgcgcgt     2280
gttcgatttg cggtgggttt ggattgggtt tggattggct ttgtatgtat gtatgtatgt     2340
atgtatgtat gtatgtatgt atgtatgtat gtatgtatgt atgtatgtgt ctatgtatgt     2400
atgtatgtat gtatgtatgt gtctatgtgt gcatgtgtgc atgtgtctat gtgtctatgt     2460
gtctatgtga ggtttgggca gtgtggtgag aggcgccatg ggcgccgtgg gtttcaggac     2520
acggtgtctc cctgggaccg gacctctccc cgttgactgg ccgggactcg ttgaccatca     2580
gcctgatgtg gcgcggccct cgcctcccgc cctacttcaa attcaaattt cccgccctcc     2640
gctgtccggc tcctacccccc ttattgaacg tttcgacagt tgattttcct gagctggctc    2700
ctccttgtat cattagattt cgcttcaccc tttcgctctg ttccgctcta cgccccgcct     2760
ttgctgcccc tcctccccgc tccctagtga caaggagcac agcaccatca tctacgaaag     2820
cccccagccc gacacgccgc tgctgagact gggctggaac cggcaggacc ccaggtacat     2880
ggccaccata ctcatggact cacccaaggt gaggggaagg gagaggggga ggggccccta     2940 aggggagca tggagggcat gcaacgagca aaacttactg gaaattagca tccccagtgc     3000
ggcagcaaag ccgggaggag aggccggagg aaagcctgca gcagcagcag cagcgcgcgt     3060
cccaagtacc aaaacattcc atatattacg tatacgctttt ctgcacctgt atgggggtgt    3120
tgtgtagtgt tgtgatttgt gatcgtacgc gcgtatttgg taaccccccc tcctgctgtc     3180
cggcgcaacg ccccatcgtt gctttgctgc ctggacgtgt atattccctc tgtcccgtac     3240
gttcccgggt gccttgcacg taggaattcc ctccccctc atttccccac cccgtgtgt      3300 gtgtgtgcgt gtgaacccct tacccccccac ccccacccc caggtggtaa ttctggatat     3360
ccggtacccc acgttgccgg tggcggagct gcaccgccac caggcacccg tcaacgcact     3420
ggcctgggcg ccccactcag cacaaacacat atgtaccgcg gggacgact cgcaggttgg     3480 gaggaggggg gcgggacccg tgggtcggtg cagggaagga tggcgccacg gatgggaaca     3540
```

| | |
|---|---|
| cggaagggcc gatattattt gctgttgatg ctacatttgc aggtgacata tggcccgagt | 3600 |
| tggcgttttg ccggtgtgtg tgtgtgtgtg tgtgcgtgtg tgttatcccc gtatgtgctg | 3660 |
| ctgcacgctg tactgtactg ccccgggtgc tcgtcgaggc ggtcgatccc tcggcacgca | 3720 |
| tcctcgcggt ttcttgcata tgattcccag ttccctccc cgtccccctc ccgtctcgc | 3780 |
| tcgcaggcgc tcatctggga cgtctcagct gtgggcagtg gcggtggtca gccggggggcg | 3840 |
| ttagggggg gaaccgcggg ggatgtgtcc ctggatccca tcctggcgta cggcgcacag | 3900 |
| agcgaggtac ggcagagcag aggggatgaa actagaagtg ggtggtcagg aggatggagc | 3960 |
| taatgaacag actgtgcgga agggttctgg agttcggaat gaatcagctg gtactgggta | 4020 |
| gtagctggtt ccgatgtggg taccaggtgg tggtcggttc ggcaggtggg cgacagcggt | 4080 |
| gtcgtggggc gccgtggaac acatccagct atcttcccg gttaatgagg gcttgggtcg | 4140 |
| cattttcttt ggcggggttt catccacagt gattggattc tttggaggag tgcaggccag | 4200 |
| gtagcgcgct ctgcatgatg tgaatgaaca gtgtggtgca gcgcagctct gttgcaccac | 4260 |
| ccacagaaag ctgcgtcgag cctcggcgcg aatacacgtg tgggctacca ccattgccct | 4320 |
| gcattgcagt ccggggatgt gggacgctca tgcagagaaa aaagctgaac cgcctttctc | 4380 |
| cccaatcggc cgctggggga cgcatgcagc tgatgatgct gccgtcctgc tgccggcgtt | 4440 |
| gtctgtccca caacacgat ctgccccctt ccgtaaccct gtctgtctgt ctgtccgccc | 4500 |
| ttctatcctg atgttttggg ctgccttttc cttgcaggtg aaccagctgc agtggagctc | 4560 |
| cgcgcagccc gactgggtgg ccatatgctt cgccaacaag acccagatcc tcagagtgtg | 4620 |
| accctgtgg gacctgcggc gacttggcta ggcttggata actcagcggc tgcgactttg | 4680 |
| cccatgtttc gcactcccgt agtgcagatg gcacgagtgt gggggcaggc aggatcaaca | 4740 |
| gcgtcgcctt gcctcaggcc acatgactcc gccatgtctg ggtgtgtagg tccgcgggcg | 4800 |
| ctgcataaaa aaagcaatcg tggcattgga gagcgcggat gcgtgccgaa aaatcttgcg | 4860 |
| ttttgcccga gggctgatgg gtcctgggtc gaggaggaag ggtgcggtta gagaggactt | 4920 |
| tcacactgaa tggctttctt tgaggagccc tcgacccctg tatgcaaatt tagcctcccc | 4980 |
| gtccacaagg aggcatgctg cggcttttg cggcaagctg tccaaaatgt ggcatgcgta | 5040 |
| ttccagagga gttttggatg taagcaggtg gaacctggg | 5079 |

<210> SEQ ID NO 20
<211> LENGTH: 3272
<212> TYPE: DNA
<213> ORGANISM: Chlorella variabilis
<220> FEATURE:
<221> NAME/KEY: misc_feature
<223> OTHER INFORMATION: WD40 repeat protein

<400> SEQUENCE: 20

| | |
|---|---|
| gtgaactcgg ccggttgcca tccaggagag agccaacccc tgagcccctg cacgggtgag | 60 |
| gaccgtcgga ggaaggcgca gaatgccggc gcggggcgcc agagcggggg agtgcgggcg | 120 |
| ccgaccgccg cccagcagca gcagcgccgg ccgcttagca gcagcgcctt gtgggggggtc | 180 |
| gtgcgcttat ctcctcgcat tctctcttac aggctcccat gcaggaccag cagcagcagg | 240 |
| gggaggggcg ggcagagatc tacacctaca gcagctcggc cagcgtctac gcctgcggct | 300 |
| tctcggtgag cagccagcca atggcagcgg ccgccgtcag ctcttccagc ccagagtgca | 360 |
| gcacaggcag cgcaggcagc gcagcacgaa gtctcagagc atgtcggccg ctgcgctgca | 420 |
| gccgtgtgcc cggcagctta ccgccactct cgccgctccc gccgctgcgt gcctcccttg | 480 |

```
cagtcccgcc ccgacaagcc cttccgcctg gctgtcggca gcttcatcga cgactatgca    540
aacaaagtgg agatcatcca gtgtgagtgt ctgtttttag gcaggcgctg cgctgcacgg    600
actgcggatg gcacggtgct gccgcggctg ctgtgattgc acgcggctgc tgctcgggtc    660
tggcgccgcc gctggggtgg gatcttgtct ggctctggct ctggatcttc atctggggcg    720
cagtcttggg catgtgggtg gtagcacgct gctcagacca ggccccacct gccgccacca    780
ccactgccta tgcgcgccac ccgcagtgga cgaggcggcc ggggtggtgc gcaacaaccc    840
tgcgctgacc ttccagcacc cctacccgcc caccaaggtc gccttcatcc cggataaggt    900
gaggcgccga ggccgggctg actgagccag gttgtgggct gcctgccggg acaaggcagc    960
agcctgcggg tgctgtcctg cccctgcccc tgacctgacc gtgctgcccc gtatgctggc    1020
tctgtgatcc ccgccttctg aacgccacca cctgccgccg ccgcctcctg ccccagagcg    1080
ggacccgccc cgacctgctg gccactagcg gcgacttcct gcgcctgtgg cgtgtgtcgg    1140
atgagcccgg ggcgcagcag ggcgtgcgcc tggagaagct gctgaacaat gtgagggcgg    1200
gcgggcgggc ggctgcgctg caggggggtgc tcagcgaggg tggagcagg ggtaggggcg    1260 cctcggtgcg gcgagtgccg gcagggctgc tggggagcga cgtgccggcc agtgtacaga    1320
gcgcaccctc gccgccagcc ctcgacgcgg cgctcgcacc acctcacacc ctgccgtctc    1380
cctctctccc ccatgctccc atgctcccat gctccccttc ccgcccgcca cccgccgcag    1440
aacaagggcg gcgactttgc ggcgccgctg acgtcctttg actggaacga gctggaccct    1500
cgccgcgtgg gcaccgcctc gatcgacacg acgtgcacgg tgtgggacgt ggagcgcggg    1560
gtggtggaca cgcagctcat cgcgcacgac aaggaggtgg gtgggtgcgg gcgggggggt    1620
gtagtgtggc cacgggcgtg gcgtgcctgc ttgtgggtgg agcatggggt ggtggtcagg    1680
ccgcagttga ttgcgagcta caaggggtg ggtggggtgg tggcttctct aggcggtgct    1740
ggtcctgtgt tcagccatgc gcttgagcat atgtgcacac cgattgcatg gagggtgtg    1800 ggcgtggtgg ggcatcaaca tcacacctgc ctgcccctgc ccgcccctca aagacctcgc    1860
tgccgcccgc ccgcctgccc gcctccccca cacacatcta tgccaggtgt acgacattgc    1920
ctggggcggg gtcgggatct ttgcctcggt ctccgccgac ggctcggtgc gcgtgtttga    1980
cctcaggtgg gaacagccgg ctcacccgcc agccgggctg cgtgcccgcc tgcccagccg    2040
cttgccctcc ggcgcagccc gtgcacactt ctgcgagctc cgccgccagg ccgcaaaccc    2100
acgcacgctc gtggccccgc cagaaaccca cgcacgcacg ctcacccgct tgcgcatgca    2160
tgcacttatt gttgtttgcc cacagggaca aggagcactc caccatcatt tatgagtccc    2220
cccagcccga cacccccctg ctgcgcctgt cctggaacaa gcaggacccg cgctacatcg    2280
caggtgcggc gcgccggcg cggggcctcg cggtaccatc gtgccccagc cgagctgcct    2340
tgcggctgct caggcccagg cacacaggca ctcaagcaca ccaccacaac caccacagcc    2400
accactttca cacccacgca cacacaagcc gttccttccc tgcgtgcagt gttagccatg    2460
gattcgccgc gggtgacggt actggacatc cggtacccca cgctccccgt ggccgagctg    2520
cagcggcacc aggcgggggt caacgccatc tgctgggccc ccacagcgc acccacctg    2580 tgctccgcgg gcgacgacag ccaggcgctg atctgggacc tgggcctgct gggcacgctg    2640
gggcagcagc ccgagggcgg cccgccgggc gccggcgg cgggtggcgg cctggacccg    2700
atcctggcct acaacgcagg cgccgaggtc aaccagctgc agtggagccc cgcccagccg    2760
gactgggtgg caatctgctt cggcaacaag acccagctgc tgcgggtgtg aggcgcgtgc    2820
cgacagagca ccacaccgcc gcgctgctcg ccggctgcag cgttgctcgc cgctcccctc    2880
```

```
cagggcagcg cggcgcccgc gccgttcctg cttcccaagc tgccagcctt cttgcgtccc    2940
ttattcgcct gctcccsctg tcttgcttcc gctcctgctg tactgccccc cgcccgcatc    3000
tgtatcaccc gggtgccttt tcttcactgc acacgtacca ccgcatctgt ggcaccctgc    3060
ccctccctaa tgcacggccc tctggcacgc tgccagcccc tctaatgcat gggccctgcc    3120
attcacacca atcgcatcaa ccgtacatct gtcccctgc actgctcttt gtcaccattc     3180
cacctgatgc tctctcctct cccaacccaa ctgatccccc cgtcgcatcc ataccgattt    3240
cgagagacac cttgcaatga aacacgcagc gc                                  3272
```

<210> SEQ ID NO 21
<211> LENGTH: 3032
<212> TYPE: DNA
<213> ORGANISM: Parachlorella sp.
<220> FEATURE:
<221> NAME/KEY: misc_feature
<223> OTHER INFORMATION: WD40 repeat protein

<400> SEQUENCE: 21

```
atgcagcgcg cagaaatcca tacgtacgag agccccacgt tggtttatgc actcaactgg      60
agtgtaagtc acacaatatg ttgacaagat actgaagcgc acatgtata ggctgtgtcc      120 tgaagaggca agctttcacc tgctgtaggt gcggcctgac aaaccsttca gactagccat     180
cggaagctac atcgaggact acaacaaccg agtggaaatc gtcacacgta tgttcaccgc     240
ttcaggtctt gctgctattg cgttcgtgcc ttcaaagtca gactttcgaa gcaagtttgc     300
ccaccggggg tctctggtgc agtcggtgaa gatggaaatg gaatgcggcc tagcccacgg     360
cacacctttc agcatcccta tccacccacc aaacttcagt ttgtaccaga tcctgatggc     420
tcccggcctg atctgttagc cagctccggt gacttccttc gactctggcg catcacggag     480
gacggggttt ccctggaaaa gcttctcaac aacgtgagcg cgcctgctct gatagcgctg     540
tcctgttgta ccatggacgg ctagcgcaca gcggtagcgc gcagtgcaac gaagacgacc     600
ggggctgacg ctactctgaa tgcaaccacc ttgcctgctg tggtgcagaa caaagcaagc     660
gagttttgcg cgcccttgac cagctttgac tggaatgaga acgaccccaa gagggtgggc    720
actgccagca tcgacaccac ctgcactgta tgggacatag agaagggggt ggtggacacc    780
caggtgggtt gagtggagta gagtggagtg gcggagaacc tggaagagca ggccatgacc    840
agggcatgcg tgctgagcac tcctgccgcc gccgccgtcg cgtcaagtct tggccgttca    900
aagactcgag gtccttccgg tgtgctgctt ggagtcgccc gcgtcctgcc acatcgtgtg    960
cctgctgccg cttttggagcc atgctcccct tgccacgcgc tcacccttgg aaccgtgtgg   1020
cccctgcagc tgattgccca tgacaaggag gtgtacgaca tagcatgggg gggcgtgggg   1080
gtgtttgcct cggtgtcagc agatggctcg gtgcgggtgt ttgacttgag gtaggtgctc   1140
tgcctgcggc cttcgacctg gggctgagtg accgggtggg gccggcctgg aggatggagg   1200
gtggaatatg gtgcagtacg cgaggtacat gatcttggcg gtggctcatc ctggtgtggg   1260
tcgctggtag aagaagcggc gtggaacagg tgtaggtgtg gggcttggag cagtgaggtg   1320
caagccagtt gtagagtatg ccccagcagc ctccccaaag ggcctcagc ccgcagcacc    1380 ctgccagcag gagcttcccc agttgctgcg ccaggggcag cgcatgctcg ggcgcacagc   1440
tgtgtgtgtg cacgacagag ccagctcctg gtgtggagct ggcggtgggc acgtgtggga   1500
gggctctgtt ggggtcccat gcgttagaca gggcatggca ggggtctggg cgtgtgggca   1560
ggtcgtgctt ctgcctcatg cgcccctccac ccaccctcac cccgctgctg cctcatacgc   1620
```

```
cccgcaccca cccccctcccc ccttcctgcc gctgcctcat gcgccctcca ccaacattcc    1680
ctgcagggat aaggagcact cgaccatcat ctatgagtcg ccgcagcccg acacccccct    1740
gctgcgcctg gcctggaaca agcaggaccc gcggtacatg gccaccactg ccctcaactc    1800
ctccgccatt gtggtgctgg acatccgatt ccccacggtg ccggtggtgg agctgtccaa    1860
gcaccaggtg cgatatggca gcggggggtgc agtcgctgcg gggggtgcct gcaatggggc    1920
agctgctatc tgccgccttg ctgtgagctg gcctggcgct gggagccagg agtgctcacc    1980
ctgctgcgag cgctgccacg ggttggctgc atcgcacagg ctgaggcccc cgggctgggc    2040
tggaagggcg ggtgcctcac cggctcaggc gcccacgagg atcgccgatt tcctgccctg    2100
gcctggtgat catgccgctg gcggcggtgc ggtggcgtgc gcagcatgcg gctgcgcact    2160
gcattggcca gccacgctgc tcgtgccatg gtgtgcatgc agcccgcacc agccaaagcg    2220
tgctcgcgct gcccgctgct gaacagacct ctcaacgcgc tccctccctc tgtggctagt    2280
gtgccccagc accaggtggc agctggagcg cgcccagcat ggtgcagcaa caggaggaaa    2340
gccgccgccc ctgggcctgc gggcaatttt agcgcgttgc gctgcgctgc attcctcgca    2400
acgtgcacgt caccgaagcg tgtatctccc cccttcccca ctgcctgcag gccgcctgca    2460
atgctgtggc ctgggccccc caaagtgcca accacatctg cagtgccggg gacgattgcc    2520
aggtggggcg cgctggaagg ggggaaggaa aggggagggg gggtcctgtg aactgggcag    2580
aatgctggcc tttctaataa accgccacca acaagctggg gctgtgcttg gggagggcgg    2640
gggcagtcgt ccccgcggc acgggggccg acacccttgc cttcccttgg cgagtattcg    2700
agcacgggac cccttcctcc cctcctgtgc atctcatgtg atgtactcgc cgagccctct    2760 gccctgctg cgactgtcgc gcagctgcaa ggccacgcgc caagcgcatt gcggcgctgt    2820
ccctccgcgc ctctgtgccg tgcgtgcagg cttttgatctg ggacctgtcc actctggggg    2880
agggcggcgc gggccaggcg gggagccccc ccctggaccc catcctgtcc tacatggcgg    2940
gggcggaggt gaaccagctg cagtggtcgg cgtcccaccc cgactgggtg gccatctgct    3000
ttgggaacaa gacgcagatt ttgagggtgt ga                                  3032

<210> SEQ ID NO 22
<211> LENGTH: 1045
<212> TYPE: DNA
<213> ORGANISM: Picochlorum sp.
<220> FEATURE:
<221> NAME/KEY: misc_feature
<223> OTHER INFORMATION: WD40 repeat protein

<400> SEQUENCE: 22
atgtcgactg attggttggt tgtaattgtg cagtctaggc aagataaggg tgtacgagta      60
gctgttggca gttttgtgga gggtgtctcg aacacagtcg agattcttcg cggtacggat     120
catctgtgag tctctgttct acttgggaaa tgtgggcata attttttgta tatgaggtgc     180
agtgactccc gcaggtttaa ttgtggatga caaggaaacg ttcggcatag agtatccggc     240
gacgcaggtg ggatttattc ctgataggtt ttgcaacaag ccagatttgt tggcaacctc     300
tggggatgct gttaggttgt ggaaaatttc agacgcaggg acgacgcttg aactggtgtt     360
gaatgatcca aagaatacct ctaaaaattt cagtgcggtg acctgctttg attggagtga     420
aatcaatgtg aaagtgttgg cggcagggtc gagtgcaggg cgattattgc tgtgggacac     480
cgagtcaggg aggctgcagg gcacaatggt gggacatgag gatgagattc ttgattgtca     540
gtgggcagct aatgatgtga ttgtttcttc ttcgggcgat ggatcaattc ggatgtatga     600
```

```
cctgcgggat aaagaccatt gcacggtatt gtatgagacc cccaggagga cccctgtgcc    660
gaggttttgt tggaacaagc tggatccgag gcatcttgca ttttctatag aaaagagtcg    720
gcttgttagt gttctcgatg ttcgctttcc gacagagccg gtgatcttgc tggacggtca    780
tatggggaac tgtacagcac ttggttggtc ccctcacaga gaggaatacc tctgctcggt    840
tggagatgat tgccatgcat tgatatggga cgtggggaag gtgaatagtg aggaggatag    900
taagccaaat cgagaggcgg tggacgcatc tcctatccta gcgtacaatg ctcaggcaga    960
gatcaatgcg atggcttgga atccaataga cccagattgg attgccattt gcgctagaaa   1020
cagaacacaa gtattgagaa tatga                                         1045

<210> SEQ ID NO 23
<211> LENGTH: 2857
<212> TYPE: DNA
<213> ORGANISM: Tetraselmis sp.
<220> FEATURE:
<221> NAME/KEY: misc_feature
<223> OTHER INFORMATION: WD40 repeat protein

<400> SEQUENCE: 23
atgccgacga gcgacgcgac gcaggcacat gagcaccatc acgtgccgca cgcgcggccg     60 cgaccccgc caagaacgtt gtctgcatgt gccatgttga tgagcaagga gaaacggcgg    120
cgccacgcag acaagagctg gccgattttt tggccagtgt gtgtgtggct agctttcgcg    180
agctccacca agaaagcctc agcgtgcggg ccagctcgct ttgcataatg cttcggcaat    240
ttgattgttg actagccgct acagtacatg tacaacggag cgtcgcctac gggtatacgg    300
agggcttgcc gtaactgtgg atcgctgcct attaaacggc cgtcgtaaag atagacgctg    360
caagggtttc actggtgtca gtcctgtccc ggggggcggga aaaccaaaac cctggtcgta    420
aatgagacgt ggcaaagttt caccggcgcc agtcgcgtat ccaggaaaaa aaaacccgcc    480
ccctcgcact cttcgtggcc acaggtagag gactgccgaa gtgatcaccc cacagcaaag    540
cccaccgtcg tcagcgctac ccgttacgtg cgggtactca gactctcgcc gcgacaccca    600
cgcaacaagc caacaacgcc gccccgcttg cggatcgctt cacgctttggg ctggtgcgga    660 accttgttca gggaccttgt tcccgccgac aaattattgc tgctcggctc tcctgcactc    720
cgacagcgtg gcaccaggct ggcctgttca ccgcccgggg ccggtgtggg ttgtggccca    780
cgcgagtggc cactcgggtt cctttcagcc tacgctgggc gtaaagccct taccagcatg    840
cttgtcctgc acgcgccccg tgctgccacg ggctgacgca ctgatcctgc cgtgttgcgc    900
ttgtggcggc aggctcggtg ctgtgccccg ggcgacgcgc gcctgggtgg gctagcttgc    960
gatggcgagc gggccggagg accggggtgc ggggcggcg ggggcggcgc ccaccaacg    1020 aggcgatagc aacggcaaag cggtgacaga caagcgcggg gagatataca cctacgaggc   1080
gccgtacccg gtatacggga tgaactggag tgtgcgtgcg ccggacatgg ccaaggggg    1140 ccaggggagg cccccccggg gggggggggg gggggaggagt tacttggtac aagcagactt   1200
tggccccgtg gctgaggggg tcgagtgttg caggtgcggg aggatatgaa gttccgcctc   1260
gcggtgggaa gctttgtaga ggacgtgag aatgcggtgg agctcatccg gcgtgagtgc   1320
ccgagcgcgt acgcaggcct gcctgctgtg tgcagggagc gcgcgggcat ccgcctgatg   1380
acgtgctgtg tgcacagtga acgaggaaac cggcaagttt gagagcaacc cggcgcacaa   1440
gtttgtgcac ccgtatccac ccaccaaaat aatgtttatc cccgaccgcg actgctcgcg   1500
ccctgacctg ctcgccacca cgggcgatta tctgcggctg tggcgcgtgg aggaggacgg   1560
```

```
cgtcacgctg cacaagctgc tgacaaatgt gagcgcggac aaacctttgt gcccgccccc    1620
cccccaccac caccagtcct ccttccctct aaggcccatt ctcaagagat accacggcca    1680
gctccagcat gacccccgcc ccctatttc gtcaacatgc acctcccccc tgcagaacaa     1740
aaacagtgag ttttgcgcgc cattaacatc ctttgactgg aacgaagccg acccgaggca    1800
actgggcacc tcatccatcg acacaacatg cacaatatgg gacatcgagg tgggccaggc    1860
agtccaagcc ccccccccc cccccccccc gcaaatgccc tccttgcgct gacatgtcaa     1920
aacgcctgcc tcgtggtgcg tccagagagg cgttgttgac acgcagctta tcgctcacga    1980
caaggaggtg tacgacattg cgtggggcgg gcagggcgtc tttgccagcg tgtccgcaga    2040
cggctctgtg cgagtgtttg acctccggtg cgccctgcgg tacctgcggc gcgcgcgac     2100 cccacctggg cgccgtggct ggcttgcggg gggggggggg ggggggctga cgcgccggcg    2160
ggctgttcgg caccgcaggg acaaggacca ctcaaccatc atctacgaga gcgggatgcc    2220
cgagatcccg ctgctgcggc tgggctggaa caagcaggac ccgcgctaca tggccaccat    2280
cctcatggac tcctccaagg tggtcgtcct ggacatcagg tccgccgccc ttgcctgcca    2340
tcacgcaaca tatactgggg gtgtgtctgg cggcgctgac ctgtgatgct gcgccgccgt    2400
gcctgctgca ggtaccccac gatgcctgta gctgagctgg aggcgcatca caagcctgtg    2460
aatgccctgg cgtgggcccc gcagtcctcc tcgcacatct gcactgcggg ggacgacgca    2520
caggtgtggc gggatgcatg ctctgatgca tcacaggaga cagagcgaca ggggggggt     2580 gagcaggggg ggggggggg ggaaggggg atgcccgggt gaggcagatg gtggctgact      2640
gttgcatgct gccgcccagg cgctcatctg gaaccttgcg cccatgggca cccaggggcc    2700 catgggggt gctgcgcctg cagttctagg cgcggacctg gatcccatcc tagcgtacaa     2760
cgccggcgag gaaatcaatc agctgcagtg gtccagcacg cagtccgact gggtgggcat    2820
atcctttggc aacaagatcc agattttgag aatctag                             2857
```

<210> SEQ ID NO 24
<211> LENGTH: 1431
<212> TYPE: DNA
<213> ORGANISM: Ostreococcus sp.
<220> FEATURE:
<221> NAME/KEY: misc_feature
<223> OTHER INFORMATION: WD40 repeat protein

<400> SEQUENCE: 24

```
cggtcgacgc gctcgacgcg gtcgacgcga gcgaggcgcg cgcttcgagc gacgcgaagg      60
cgtcggacgc gaacgcgaag gcgtcgagcg cgaacgcggg acccgacggg cggtgaaggc     120
gcgcgacgaa agacgaggaa ggcgcgcgcg aacgatgaac gcggagaaga gggcggaaat    180
atacacctat gaggcgccgt ggatgatcta cgcgtgcaat tggagcgtgc gtggcgagcg    240
aggcgatgga ttgggggcga gcgcgggaga attgaatcgc gaggggcgac ggaggagacg    300
cgacggagga gactcgggga cgcgcgcgaa cggtcgatcg gagattaaaa atggagacgc    360
gcgagtgaag acgcgaatgg cgtggactga cgacgtcgaa ttgaacgcga caggttcgac    420
aagataaacg cttccgcctc gccttgggtt cgttcgtgga ggagtatagc aacaaggttg    480
agatcatcac cttggacgag gaaaccgggg agtttccgaa ggaggcgcag tgttcgttca    540
cgcatccgta tccttgcacg aaaattttgt tcattccgga caaggagtgc acgaaggagg    600
atttgttagc gacgacgggg gactacttgc gaatctggca agtgcaggat gataacacgg    660
tgcagatgaa atctttactg aataataaca agagcagcga attttgcgca ccgctgacga    720
```

-continued

```
gctttgattg aacgagacc aagcttcagc gagtggggac gtcgtcgatc gacacgacgt    780
gtacgatttg ggacatcgag cgcgagtgcg tggacacgca gctcatcgcg catgataagg    840
aggtgtacga catcgcgtgg ggtggtccag aggttttcgc tagcgtaagt gcggatggaa    900
gtgtgcgagt tttcgacttg agagacaagg atcacagtac gatcatttac gagagtcaaa    960
ctccagacac gccgctgctg cgtttggggt ggaacaagca ggatccgaga tacatggcca   1020
ccatttgcat ggatagtccg gtgatcattc tcgatattcg cttcccgacg ttgccggtcg   1080
cagaacttca gagtcacaga gcgagcgtga atacattggc gtgggcgcca cacagctcaa   1140
gccacatgtg cacggcgggc gacgacagtc aggcgttgat ttgggatttg tcgtccatga   1200
atcaaccacc cgaaggcggt ctcgacccta ttctcgctta ctctgctgga gcagaaatca   1260
atcagttaca gtgagcgcg tcgcaaccgg attggatctc gatagctttc cgaaacagcc   1320
tccagatcct ccgagtttag tcaacgcgct gtcaggtctg cgccgacgcc actgtatatt   1380
acccgaattt ccggatacgc gacacacgac acacgacacg cacgcacgta g            1431
```

<210> SEQ ID NO 25
<211> LENGTH: 1294
<212> TYPE: DNA
<213> ORGANISM: Micromonas commoda
<220> FEATURE:
<221> NAME/KEY: misc_feature
<223> OTHER INFORMATION: WD40 repeat protein

<400> SEQUENCE: 25

```
atggcggcca tgggcagcgg ccagagcggc gccgagattt acacgtacga ggcgccatgg     60
ctcgtgtacg cgatgaattg gagtgtgagt gcccgtcgat gactctgctc cgtcccgccg    120
cgttcctccc cgcccgggcc gatccctcgc ctgcacccaa tctgacccgg caagatccgc    180
tgctgacgcg actttgagga cgcgccggc agtcgaccga cgcgccccgc ccgcgacgt     240 gacccgctga cgcttcactc gatataaacc tccccctccc cgcgcgcgca ttcaacaggt    300
gaggcaggac aagaggttcc gcctcgcgct cgggtcgttc gtggaggagt acagcaacaa    360
ggttgagatc atcacgctgg acgagcagcg acggagtttt ccggcggagc cgacgcacag    420
gttcgaccac ccgtacccgt gcacgaagat catgttcgtc ccagacgccg agggaaccag    480
cgaggactta ctggccacga gcggcgacta tctgcgggtt tggcgcatag gcgacgacgg    540
cgtgcacctg cggagcctcc tgaacaacaa caagaacagc gacttttgcg cgccgctcac    600
gtcgttcgac tggagcacca ccaacctggc gagggtgggc accagcagtt tggacaccac    660
gtgcaccatc tgggacctgg agaaggagac ggttgactcg cagctcatcg cgcacgacaa    720
ggaggtgtac gacatcgcgt ggggcgggcc ggaggttttc gcgagcgtct ccgccgacgg    780
gagcgtcagg gtgttcgacc tgcgggataa ggaccacagc acgatcgtct acgagtcccc    840
gacgccggac acgccgctgc tgaggttggg ttggaacaag cagaacccga ggtacatggc    900
gacgatggag atggacagcg ccaaggttgt ggtgctggac attcgcgtgc ccgcgctgcc    960
ggtggcggag ctgaagaagc acagagccgc ggtgaacacg ctggcgtggg cgccgcacag   1020
ctcgaggaac atatgcaccg ccggggacga cgcgcaggcg ctcatttggg acctgtcgtc   1080
ggtggcgcag cccggggagg acgggatgga tccgatgctg gcgtacaacg cggggcgga   1140 gatcagtcag ctgcagtgga gcgcgacgca aaccgactgg atagccatcg cattcggcaa   1200
aaacctgcag gtgcttcacg tgtgacgccc gcggggagaa cgtggcgatc gtagtcctag   1260
ttcggttttg aattcaacgt tcatttagca ctca                                1294
```

```
<210> SEQ ID NO 26
<211> LENGTH: 1041
<212> TYPE: DNA
<213> ORGANISM: Arabidopsis sp.
<220> FEATURE:
<221> NAME/KEY: misc_feature
<223> OTHER INFORMATION: WD40 repeat protein

<400> SEQUENCE: 26
atgggaacga gcagcgatcc gattcaagat ggttccgatg agcagcagaa gcgatcagag      60
atctatacat acgaagcgcc atggcacatc tacgcaatga attggagcgt tcgtcgcgat     120
aagaagtatc gtctcgccat cactagcctc ctcgagcaat acccgaaccg tgtcgagatt     180
gtgcagctcg atgaatccaa tggtgagatc cgttccgatc ctaacctctc ctttgagcat     240
ccttatccac caacgaagac catttcata cctgacaagg aatgccaaag acctgatctt      300
ctcgctactt caagtgattt ccttcgttta tggagaatcg ctgatgatca ttcccgtgtt     360
gagctcaaat cttgtctcaa tagcaataag aacagtgagt tttgtggtcc tcttacttct     420
tttgattgga atgaagctga gccacgtcga attggaacat ctagtactga tacgacttgt     480
actatctggg acattgagcg tgaagctgtt gatactcagc ttattgctca tgataaggaa     540
gttttgata ttgcttgggg tggtgttggt gttttgcat ctgtttcagc tgatggctcc       600
gttagggtgt ttgatcttcg tgataaggaa cattcgacga ttatctatga gagctccgag     660
cctgatactc ctttagtgcg tcttggttgg aacaaacagg atcctaggta catggctact     720
attatcatgg acagtgctaa agttgtggtg cttgacattc gttttccggc tcttcctgtg     780
gttgagcttc aacgacatca agctagtgtc aatgccattg cttgggctcc tcatagctct     840
tgtcacattt gtactgctgg agatgattct caagctttga tttgggatat ttcatccatg     900
ggacagcatg ttgaaggtgg tcttgaccct attctagctt acactgctgg tgctgagatt     960
gagcagcttc agtggtcctc ttctcagcct gattgggtcg caattgcttt ctctactaag    1020
ctgcaaattc tcagggtttg a                                              1041
```